United States Patent [19]

Munsif

[11] Patent Number: 5,617,854

[45] Date of Patent: Apr. 8, 1997

[54] SHAPED CATHETER DEVICE AND METHOD

[76] Inventor: Anand Munsif, 127 E. Northfield Rd., Livingston, N.J. 07039

[21] Appl. No.: 264,069

[22] Filed: Jun. 22, 1994

[51] Int. Cl.$^6$ ............................ A61B 17/36; A61B 5/042
[52] U.S. Cl. ............................ 128/642; 606/50; 607/122
[58] Field of Search ............................ 128/642; 607/119, 607/122, 123, 125, 148, 154, 156; 606/49–50

[56] References Cited

U.S. PATENT DOCUMENTS 5,242,441  9/1993  Avitall ........................................ 606/41
5,263,493  11/1993  Avitall ........................................ 607/122

OTHER PUBLICATIONS

Jenkins, K.J. et al., "Multipolar Endocardinal Mapping of the Right Atrium During Cardia Catheterization: Description of a New Technique", *JACC*, Oct. 1993, 22:1105–1110.

Josephson, Mark.E., Ch. 2: "Electrophysiologic Investigation: Technical Aspects", *Clinical Cardiac Electrophysiology: Techniques and Interpretations*, Second Edition, 1993, pp. 5–21.

Kuo, Chien–Suu et al., "In Vivo Angioscopic Visualization of Right Heart Structure in Dogs by Means of a Balloon--Tipped Fiberoptic Endoscope: Potential Role in Percutaneous Ablative Procedures", *American Heart Journal*, Jan. 1994, 127:187–197.

McGuire, M.A. et al., "Dimensions of the Triangle of Koch in Humans", *The American Journal of Cardiology*, Sep. 15, 1992, 70:829–830.

Schetky, L. McDonald, "Shape–Memory Alloys", *Scientific American*, Nov. 1979, 24:74–83.

Swartz, J.F. et al., "Right–Sided Accessory Pathway Ablation Using an Anatomically Conforming Long Vascular Sheath Design", *JACC*, Feb. 1994, 1A–484A:277A.

Anderson, J.H. et al., "Transcatheter Spleric Arterial Occlusion: An Experimental Study in Dogs", *Radiology*, Oct. 1977, 125:95–102.

Avitall, B. et al., "A New Pigtail Type Catheter for Retrograde Atrial Left–Sided Accessory Pathway Mapping and Ablation", Abstracts from the 66th Scientific Sessions, Oct. 1993, vol. 8(4)(2), p. 0326.

Avitall, B et al., "A New Catheter for Mapping and Radio Frequency Ablation of the A V Node and Right Sided Accessory Pathways", *JACC*, Feb. 1993, 21:418A.

Cox, J.L., "The Surgical Treatment of Atrial Fibrillation: III. Development of a Definitive Surgical Procedure", *J. Thorac Cariovasc Surg.* 1991, 101:569–583.

Cox, J.L., "The Surgical Treatment of Atrial Fibrillation: IV. Surgical Technique", *J Thorac Cardiovasc Surg.*, 1991, 101:584–592

Cragg, A. et al., "Nonsurgical Placement of Arterial Endoprostheses: A New Technique Using Nitional Wire", *Radiology*, 1983, 147:261–263.

Dotter, C.T. et al., "Transluminal Expandable Nitinol Coil Stent Grafting: Preliminary Report", *Radiology*, Apr. 1983, 147:259–260.

(List continued on next page.)

*Primary Examiner*—William E. Kamm
*Attorney, Agent, or Firm*—Richard N. Miller

[57] ABSTRACT

Pre-shaped cardiac catheters for mapping and selective ablation of a portion of cardiac circuitry includes a pre-shaped first curved portion for positioning around the ostium of coronary sinus and a second curved portion for maintaining the first curved portion in its desired position. The method involves introducing a catheter assembly, including a guide-wire and a preshaped catheter, to a location proximal the atrium. As the guide-wire is withdrawn from within the catheter, the catheter assumes its preshaped form at the target location. Alternatively, a catheter assembly, with or without a guide-wire, may be introduced to the target ablation site via a catheter sheath. The catheter includes an array of spaced apart electrodes on at least a portion of the catheter. Each electrode may be activated remotely to a preselected current level for a preselected time interval to ablate a target portion of cardiac circuitry adjacent the electrodes.

24 Claims, 37 Drawing Sheets

OTHER PUBLICATIONS

Feld, G.K. et al., "Radiofrequency Catheter Ablation for the Treatment of Human Type 1 Atrial Flutter: Identification of a Critical Zone in the Reentrant Circuit by Endocardial Mapping Techniques", *Circulation*, Oct. 1992, 86:1233–1240.

Huang, S. et al., "Percutaneous Microwave Ablation of the Ventricular Myocardium Using a 4–mm Split–Tip Antenna Electrode: A Novel Method for Potential Albation of Ventricular Tachycardia," *JACC*, 1994, 1A–484A, p. 34A.

Jackman, W.M. et al., "Catheter Ablation of Accessory Atrioventricular Pathways (Wolff–Parkinson–White Syndrome) by Radiofrequency Current", *The New England Journal of Medicine*, Jun. 6, 1991, 324:1605–1611.

Jackman, W.M. et al., "Treatment of Supraventricular Tachycardia Due to Atrioventricular Nodal Reentry by Radiofrequency Catheter Ablation of Slow–Pathway Conduction", *The New England Journal of Medicine*, Jul. 30, 1992, 327:313–318.

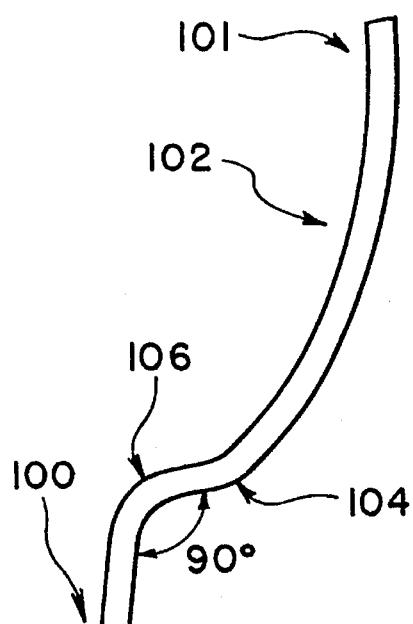
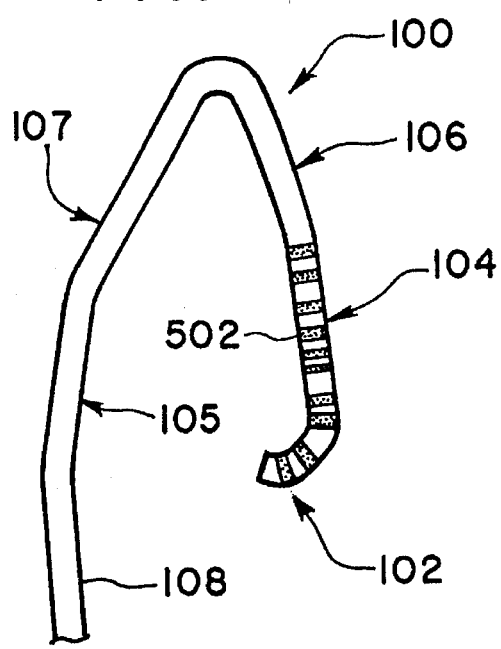
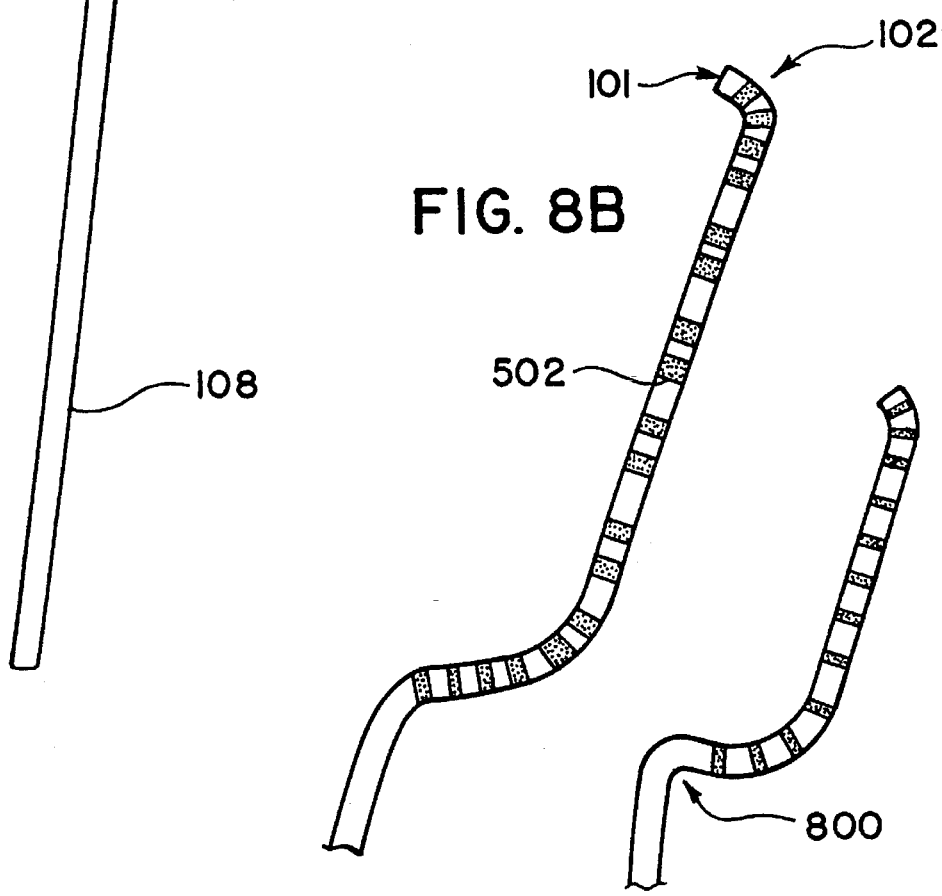

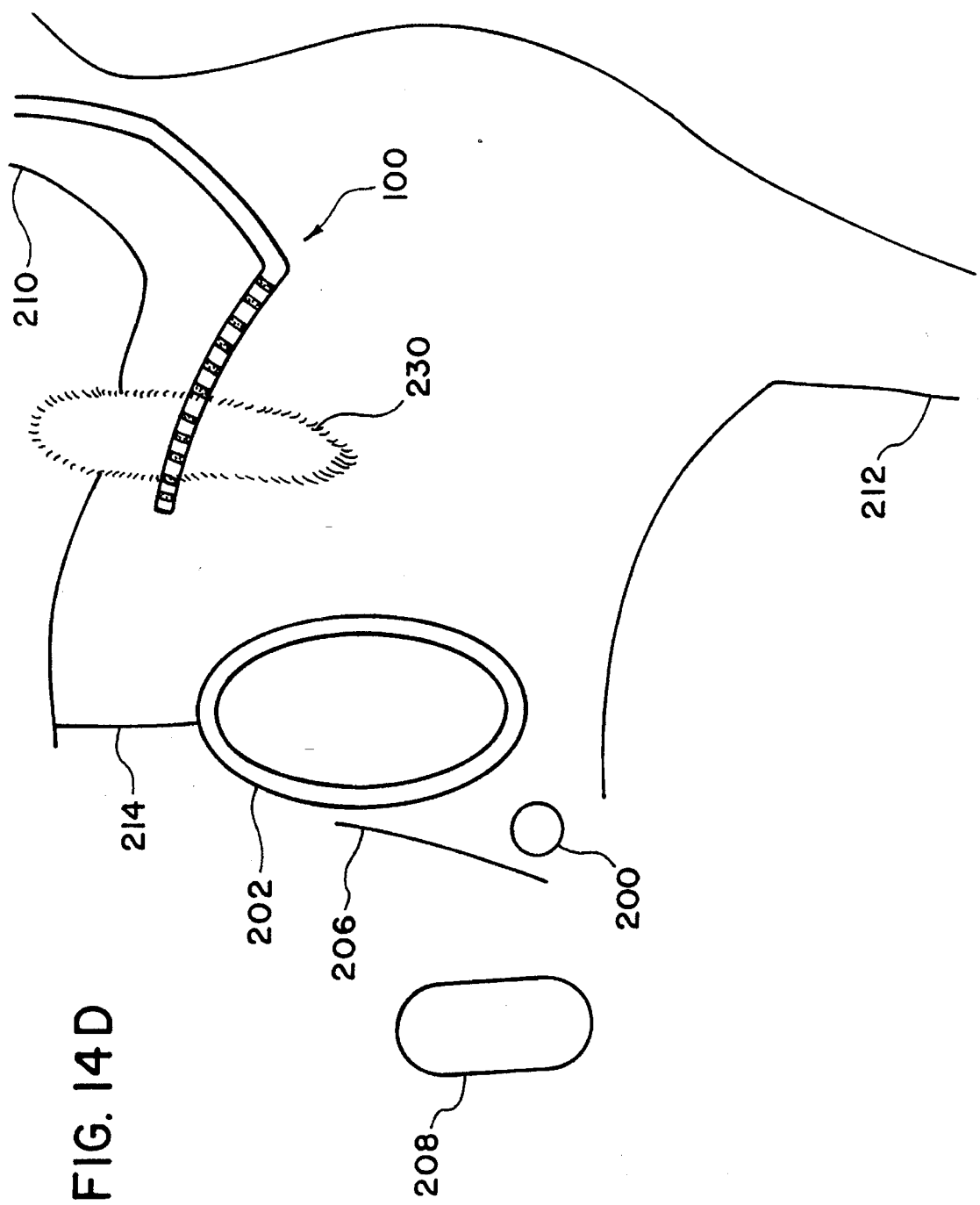

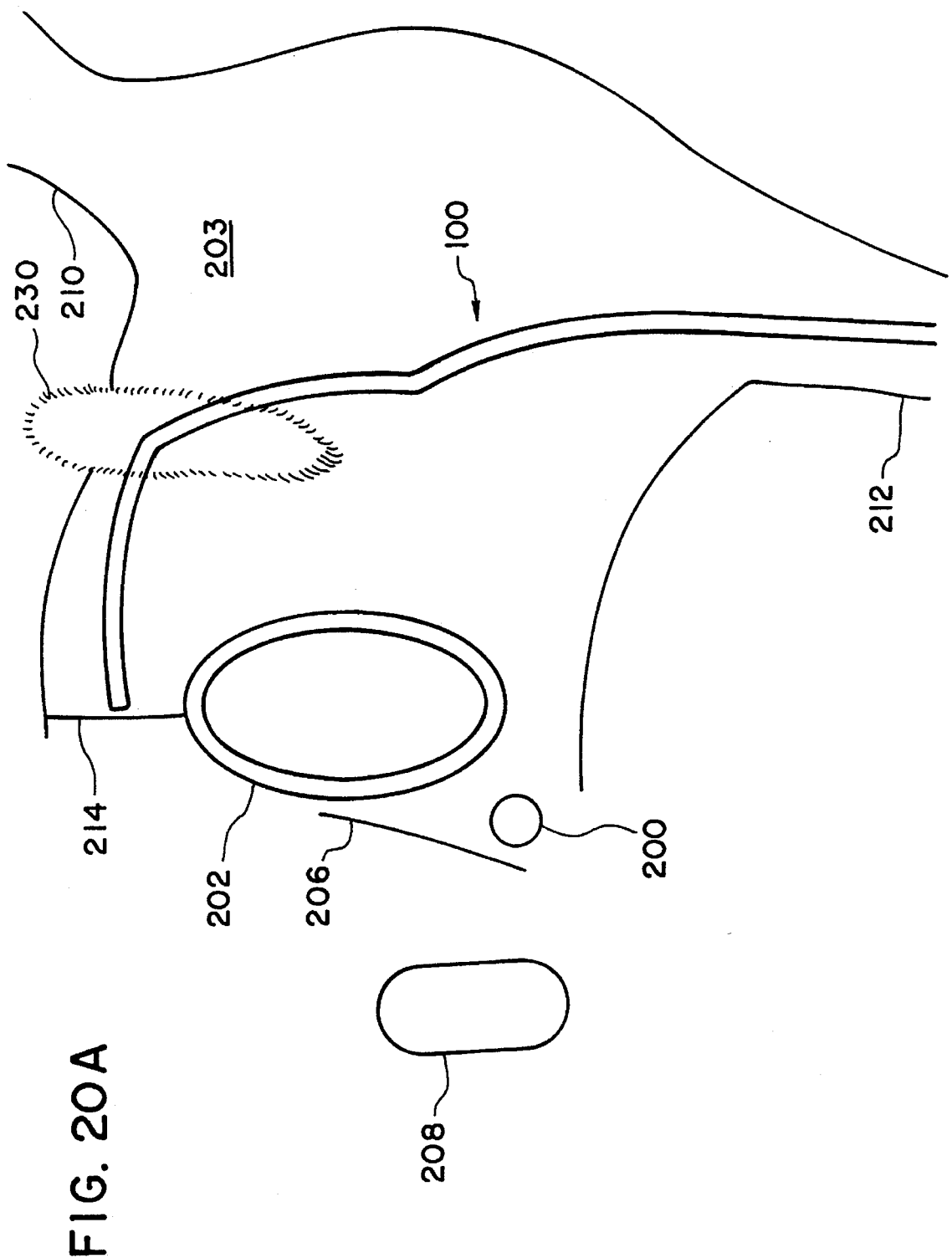

SHAPED CATHETER DEVICE AND METHOD

BACKGROUND OF THE INVENTION

1. Field of the Invention

The present invention relates generally to the field of catheters, and specifically to the field of cardiac catheters designed for mapping and ablation of selected portions of cardiac circuitry accessible through blood vessels which are contiguous with the heart.

2. Description of Related Art

Cardiac pacing typically begins with a depolarization impulse at the sinoatrial (SA) node, which spreads as an electrical wave from its location in the right atrium across to the left atrium and down toward the zone between the atrium and the ventricles. At that point, another impulse conducts through the atrioventricular (AV) node and to a common pathway, known as the bundle of His, between the right and left ventricles. As long as this basic system is intact, impulses are transmitted normally and cardiac rhythm is maintained.

The natural impulses may be interrupted by a variety of congenital or external causes. Cardiac arrythmias typically result from such disrupted cardiac pathways, and take the form of brachycardia, tachycardias, and the like. Each of these is potentially fatal. Historically, treatment for such conditions has included drugs, such as lidocaine, quinidine, procainamide, certain Beta blocking drugs, open heart surgery. The less traumatic procedure of using specialized catheters instead of the traumatic procedure of open heart surgery, has led to the evolution of cardiac catheter technology.

Cardiologists and cardiac surgeons have used selective ablation to treat certain rapid heart rhythms, such as accessory pathways of AV reciprocating tachycardia. Either cryoablation or catheter ablation was used to disrupt the electrical pathway in the heart by disrupting accessory pathways of atrioventricular reciprocating tachycardia.

Surgical ablation of the accessory pathway was used as a method for treating patients with Wolff-Parkinson-White syndrome for over twenty years. High-energy shocks delivered near the coronary sinus ostium was used to ablate posteroseptal pathways. Radiofrequency (RF) current was used to selectively ablate various accessory atrioventricular pathways to treat the Wolff-Parkinson-White syndrome by Jackman et al., (New Engl. J. Med. 1991; 324(23): 1605–1611).

Atrial fibrillation (AF) afflicts about 1.5–2 percent of the population. AF is characterized by irregular, often rapid heart beats due to uncoordinated electrical activity of atria. These cause strokes, hinting, dizziness, palpitations, shortness of breath, and reduction in amount of blood pumped out by the hear. The latter is particularly important in patients who have low ejection fraction due to prior heart attacks.

Existing medicinal treatment for AF is only partially effective at best. Recent studies have shown that there is a minimum of 1–2 percent per year risk of life-threatening proarrythmia. That is, the medicine that is supposed to treat the irregular heart beats itself is responsible for causing death due to life-threatening irregular cardiac rhythms. Thus, most physicians now believe that antiarrhythmic treatment is not advisable except under unusual circumstances.

Treatment of AF with anticoagulants reduces risk of strokes but does not abolish strokes. The ideal surgical treatment for AF results in the abolition of the three detrimental sequelae of the arrhythmia. That is, the procedure restores a regular ventricular rhythm, restores normal cardiac hemodynamics, and alleviate the patient's vulnerability to thromboembolism. (See Cox, et al., J. Thorac. Cardiovasc. Surg. 1991;101(4):569–583; and, Cox, J. Thorac. Cardiovasc. Surg. 1991;101(4):584–592) The surgical approach taught by that publication effectively treats atrial fibrillation by creating an "electrical maze" in the atrium. Atrial incisions are introduced to prevent atrial reentry and to allow sinus impulses to activate the entire myocardium. Current efforts toward finding an effective treatment for AF are centered around identifying the proper locations to cauterize in the heart so that results of the one surgical procedure known to cure the problem can be replicated in a cardiac catheterization laboratory.

Radiofrequency catheter ablation has also more recently been used for the treatment of human type 1 atrial flutter (Feld et al., Circulation 1992;86(4):1233–1240) and for the treatment of atrioventricular nodal reentrant tachycardia (Jackman et al., New Engl. J. Med. 1992;327(5):313–318). Transcatheter radiofrequency or direct current energy to treat multiple atrial arrhythmias has provided a definitive cure for many patients without the need for thoracotomy; however, consistent, successful RF ablation of ectopic atrial tachycardia has remained elusive. One author discloses a new, flexible, basket-shaped recording catheter to facilitate rapid, high resolution mapping. (Jenkins et al., JACC 1993;22(4):1105–1110)

Jackman et al. disclose a quadripolar catheter with a distance of 2 mm between electrodes, a large-tip electrode, and a deflectable curve was used for the ablation for treating AV node reentrant tachycardias. The catheter was inserted through a right femoral venous sheath, and the tip electrode was positioned at the site from which the largest, sharpest, and earliest activation of the atrial end of the slow pathway ($A_{sp}$) potential was recorded during retrograde slow-pathway conduction or from which the largest, sharpest, and latest $A_{sp}$ potential was recorded during sinus rhythm. RF current (550 to 750 kHz) was delivered at 45 to 70 V between the catheter-tip electrode and an adhesive electrosurgical dispersive pad applied to the left posterior chest. Current was applied for 45 seconds or longer but was terminated immediately in the event of an increase in impedance or displacement of the catheter electrode.

A variety of catheters currently are available having at least two ring electrodes for bipolar stimulation and/or recording. A single pair of electrodes is sufficient for routine pacing or recording; simultaneous recording and stimulation or ablation typically requires two pairs. The catheter construction may be of the woven Dacron variety, such as those commercially available from Bard Electrophysiology (Billerica, Mass.) or of the extruded synthetic materials such as polyurethane. Commercially available catheters typically are flexible enough to form loops and bends as such are encountered in the vascular system. An optimal catheter has a combination of torque control and flexibility.

One difficulty in treating abnormal cardiac rhythms, is that the tissue causing the abnormal rhythm is located in the right atrium at or near the tricuspid ring. Unlike the procedure for ablating tissue surrounding the mitral valve annulus, a coronary sinus catheter readily provides crucial information regarding placement of the catheter. Unfortunately, no such structure is present at the right side of the heart, thus most devices cannot effectively be positioned and secured at the proper position long enough to map and ablate.

One commercially available catheter is the Webster™ deflectable halo catheter, available from Webster Laboratories, Baldwin Park, Calif. That catheter includes a catheter body that is coiled in its proximal portion to resemble a halo. Once the tip of the catheter is placed into the ostium of the coronary sinus, the radius of the halo can then be increased or decreased by adjusting an attached manual control device, either advancing or withdrawing the catheter or applying torque to the catheter to turn it to one side or another. The device includes a protective sleeve to maintain its shape during shipment and storage. The catheter is available in a variety of catheter tip configurations, depending on the size requirements of the patient. Accurate positioning of such catheters often is difficult since the catheters slide in and out of the coronary sinus and on the atrial endocardium.

Vascular sheaths may be used to position a catheter at a desired position. A commercially available vascular sheath, or catheter assembly, is the Fast-Cath™ Hemostasis Introducer Swartz™SR series, from Daig Corporation, Minnetonka, Minn. That vascular sheath is designed for the introduction of electrophysiology catheters or other catheters where the varying curves and longer length of the sheath aid physician technique. The series includes several catheters having manual control over the deflection of the catheter tip position. The different sizes and configurations of the catheters are necessary due to the limited range of motion for the catheter tips imposed by the mechanics of the devices.

Catheters have been developed that have an internal lumen through which a control device is inserted for controlled rotation of the catheter tip in the horizontal plane during frontal plane fluoroscopy. These catheters primarily are used for atrial and ventricular mapping. However, the ability of these catheters to bend and rotate once inside the atrium or ventricle are limited, since a relatively stiff catheter is more easy to control remotely yet does not bend to accommodate the passageways as readily as does a more flexible catheter which is more difficult to control remotely.

Furthermore, current characteristics of ablation catheters make them difficult to position and keep on the right atrial AV ring. The tip often falls back into the ventricle, especially during the application of RF energy. One attempt to address this problem was presented by Avitall et al. (JACC 21 (2); 418A, Feb. 1993; U.S. Pat. No. 5,263,493). That disclosed catheter includes a small adjustable loop positioned at the most distal portion of the catheter ring. The catheter adapts to the shape of the tricuspid ring when opened and is capable of reducing/expanding its diameter under separate control. The small adjustable loop is anchored in the RV outflow while the other end rests on the annulus of the tricuspid valve and is anchored by the inferior vena cava.

Avitall et al. (Abstracts 661h Scien. Sess., 88(4)(2), Oct., 1993) also disclose a catheter having a pigtail shape which was set into the catheter tip at a 90° angle to saddle the pigtail curve over the mitral leaflets and into the tissue groove located around the AV ring. Both of these Avitall et al. catheters attempt to address the problem of maintaining an accurate and consistent catheter positioning once the catheter is deployed at the desired location.

Thus, there remains a need for a cardiovascular catheter which embodies a combination of torque control and flexibility for use in selectively mapping electrical activity of the heart and for ablating portions of the atrium or ventriculum, and which will remain in position once deployed. There also remains a need for effectively treating AF, atrial flutter, AV node reentry tachycardia, and AV reciprocating tachycardia.

SUMMARY OF THE INVENTION

The present invention is a group of preshaped catheters, each of which may be used for mapping and selectively ablating portions of cardiac circuitry, particularly such circuitry located around the ostium of coronary sinus. Such ablation is useful for treating certain abnormal rapid heart rhythms arising from the atrium.

Specifically, the present invention is directed to a catheter device constructed for use in persons undergoing diagnostic or therapeutic electrophysiological evaluation and treatment. The catheter device may have one of several specific, predefined configurations. One configuration includes a semi-circular curve at the distal end, adjacent a second "hairpin" curve that leads to a short, straight segment, acutely angularly displaced from a second straight segment. In practice, the first, curved portion is positioned around the ostium, or "os" of the coronary sinus, and includes a plurality or array of spaced apart electrodes on its external surface. The electrodes may selectively be activated to deliver current to selected tissue adjacent the ostium. In this manner, the circuitry is selectively ablated at the ostium.

In one embodiment, the secondary curve of the preshaped catheter is angled such that a portion of the catheter rests against the medial wall of the right atrium, and the tertiary curve of catheter is angled such that a portion of the catheter rests against the posterior wall of the right atrium. Due to the tertiary curve of the catheter, further advancement of the catheter from the groin causes the catheter to rest in contact with the endocardium. Electrodes positioned on the catheter surface permit recording of electrical activity of the heart in this area and selective ablation. A plurality of catheters thus positioned may collectively function to ablate a target area of the atrium. Effective treatment of atrial fibrillation may be achieved by selective ablation of target circuitry using a plurality of these catheters in both the left and right atrium.

In practicing the present invention, a coronary wire is introduced through a blood vessel, typically a major vein. In one embodiment, the inventive pre-shaped catheter is advanced into the right atrium via the superior vena cava or the inferior vena cava with the assistance of a guide-wire, such as a "J-wire", under fluoroscopic guidance. The portion of the guide-wire that extends beyond the tip of the catheter is positioned proximal the os of the coronary sinus. Keeping the catheter in its position at the os (i.e., "benching" the catheter), the guide-wire is removed from the catheter lumen. As the guide-wire is removed, the tip portion of the pre-shaped catheter assumes its shape such that the primary curve portion wraps around the os of coronary sinus.

Also disclosed are methods for treating certain abnormal cardiac rhythms, such as ectopic atrial tachycardia, AV node reentrant tachycardia, arrhythmias due to accessory AV connections, as well as atrial fibrillation. Additional arrhythmias which may be treated by the disclosed method include: inappropriate sinus tachycardia; sinus node reentrant tachycardia; sinoatrial reentrant tachycardia; intraatrial reentrant tachycardia; typical and atypical atrial flutter; automatic atrial tachycardia; permanent form of atrioventricular junctional reciprocating tachycardia; and, atrioventricular junctional tachycardia. The present methods include ablation of selected cardiac circuitry of the left and right atrium.

BRIEF DESCRIPTION OF THE DRAWINGS

FIG. 8A is an alternative embodiment of a catheter of the present invention.

FIG. 8B shows details of the tip portion of the catheter of FIG. 8A, including an array of spaced apart electrodes.

FIG. 8C shows an alternative embodiment of the catheters of FIG. 8A and 8B.

FIG. 9A is an alternative embodiment of a catheter of the present invention.

FIGS. 14A–14G are medial anterior wall views of the right atrium with various catheters in position.

FIGS. 20A–20G show a medial-anterior view from the inverior vena cava of the right atrium with a catheter of the present invention in alternative positions.

DETAILED DESCRIPTION OF THE PREFERRED EMBODIMENTS

The present invention is a series of preshaped catheters, one of such catheters having a first and a second curve preferably designed to securely fit around the ostium of the coronary sinus of the heart. The catheters may be used to ablate predefined cardiac circuitry around the ostium of coronary sinus for treating rapid heart rhythms arising from the atrium. These rapid heart rhythms may include atrial fibrillation, atrial flutter, atrioventricular node reentry, atrioventricular reciprocating tachycardia (AVRT), ectopic atrial tachycardia, and the like.

Description of the Catheters

Figure 1:
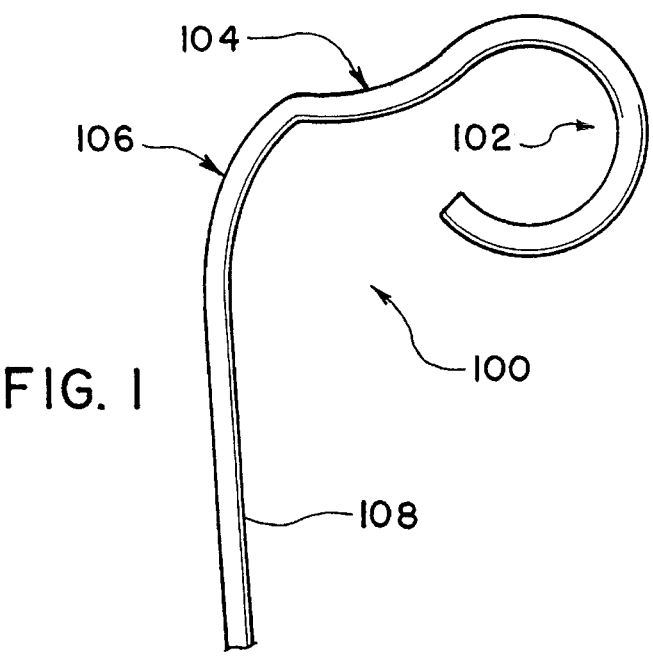
FIG. 1 is a perspective view of one embodiment of the catheter of the present invention in a shaped position.

Turning now to FIG. 1, that figure shows a perspective view of a catheter (100) of the present invention. The catheter (100) includes a first curved portion (102) which is designed to fit around the ostium of the coronary sinus (200 of FIG. 6) when properly positioned, as discussed in further detail below. The first portion (102) is contiguous with a second curved portion (104) that is designed to fit, in one embodiment, across the tendon of Todaro (206 of FIG. 6). In this manner, the second curved portion (104) assists in retaining the first curved portion (102) in the desired position around the ostium of coronary sinus. In other embodiments in which other target sites are selected, the first curved portion (102) may function to secure the second curved portion (104) in position.

In alternative embodiments, the catheter (100) may include additional curved portions which function to secure the catheter (100) in its desired location in the atrium. For example, as shown in FIG. 1, the second curved portion (104) may be contiguous with a third curved portion (106), which is designed to fit against the fossa ovalis (208 of FIG. 6). Again, in the illustrated embodiment, the third curved portion (106) functions to assist in securing the first curved portion (102) in the desired position around the ostium (200). The curved portions of the catheter terminate in a catheter shaft (108), which extends for some predetermined length, typically approximately 100–150 centimeters. It is this shaft (108) portion that the user directly manipulates.

The tubular, flexible body of the catheter (100) preferably is manufactured by extruding, biocompatible shaped memory material, such as bioinert polymers, metal strips, Dacron™, and polyvinyl chloride. In one embodiment, the catheter (100) includes a walled (112) lumen through which a guide-wire (110) may pass. In alternative embodiments, the catheter (100) may be manufactured without the lumen, in which case the catheter (100) would be used in conjunction with a sheath or other positioning aid, as discussed below in further detail.

The polymeric material forming the catheter wall (112) preferably is of the type that provides substantial rigidity to the catheter (100) when in position at the ostium (200), yet has a memory such that it may be preformed in a specific shape, deformed to position, and then reformed into its specified shape when in position. The catheter material preferably is any biologically compatible, relatively inert polymeric material having the requisite strength and flexibility to retain its shape and position within the selected atrium. Exemplary materials that may be used in manufacturing the catheter (100) include barium sulfate embedded polymers, and polytetrafluoroethylene (PTFE).

Figure 2A:
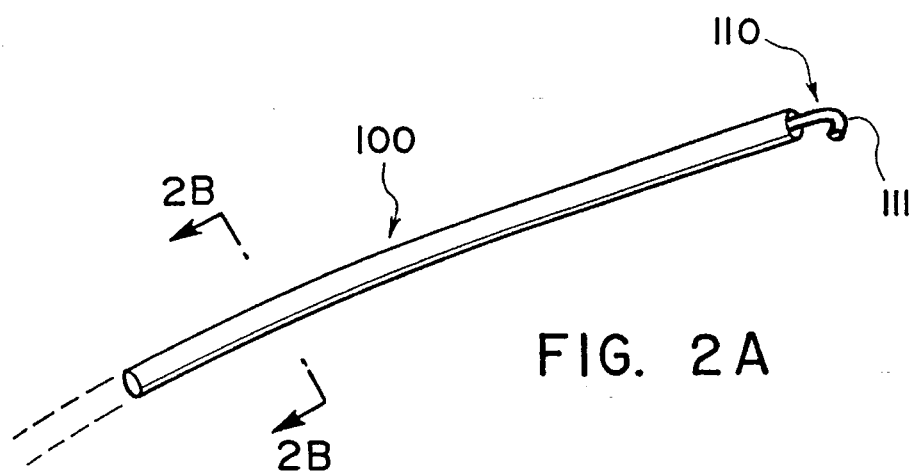
FIG. 2A is a perspective view of the catheter of FIG. 1 in a preposition configuration.
Figure 2B:
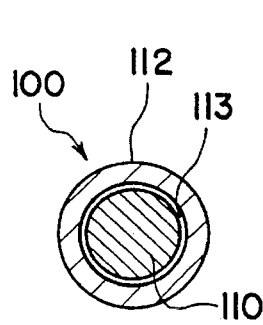
FIG. 2B is a cross-section view of the single lumen, J-wire embodiment of the catheter of FIG. 2A.

FIG. 2A shows the catheter (100) in a pre-positioned configuration. This is the configuration for the catheter (100) during its introduction into the selected atrium. In that illustrated embodiment, and as shown in cross-section in FIG. 2B, the catheter (100) includes a guide-wire (110) that passes through the catheter lumen (113) and extends beyond the end of the catheter an amount sufficient to assist the end-user in positioning the catheter (100) at a desired position. The guide-wire (110) preferably is a stainless steel J-wire of the type used in other, commercially available catheters, that includes a curved distal portion (111) to minimize potential damage to surrounding tissue, including the vein through which the catheter (100) is introduced to the target mapping and ablation site. The guide-wire (110) may be coated or otherwise treated with a biocompatible material, and may be manufactured from any bioinert metal.

Figure 2C:
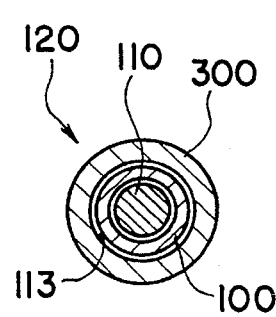
FIG. 2C is a cross-section view of a sheath/guide-wire catheter assembly of the present invention.

In an alternative embodiment, a catheter assembly (120) a sheath (300), including a guide-wire (110), is used to position the catheter (100) at the target mapping and/or ablation site. FIG. 2C shows an exemplary assembly, in cross-section, that includes a sheath (300), a catheter (100), and a guide-wire (110) nested within the catheter lumen (113). The sheath (300) may one of a variety of types, including a Mullin's sheath, commercially available from USCI, Billerica, Mass. The sheath (300) preferably is manufactured from a bioinert and/or biocompatible material.

Figure 2D:
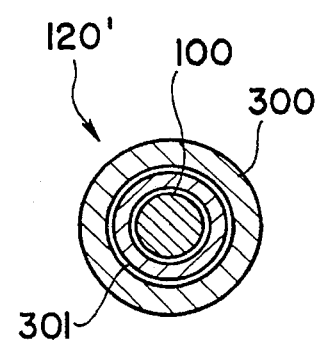
FIG. 2D is a cross-section view of a sheath/dilator catheter assembly of the present invention.

Another embodiment of a catheter assembly (120'), shown in cross-section at FIG. 2D, includes a sheath (300), having a essentially solid dilator (301) within which is passed the catheter (100). The dilator preferably is manufactured from a bioinert, solid material that retains the shape of the sheath (110) during introduction of the catheter assembly (120') into the target atrium. Alternatively, the catheter assembly (120') also may include a guide-wire (not shown). In that embodiment, the dilator (301) may be preshaped to guide the guide-wire to the target location.

In yet another embodiment, the catheter (100) may be manufactured from nitinol, which is a specially formulated alloy of nickel and titanium having a heat-sensitive memory. The alloy is described in further detail by Cragg et al., in 147 Radiology 261–263 (Apr. 1983). As described therein, nitinol can be drawn into a wire of precise dimensions. The alloy undergoes a phase change at a certain temperature. For example, the material may be annealed at 525° C. for 30 minutes while being constrained to a desired shape. After cooling, the material can be straightened and introduced via catheter sheath into the target atrium. The coil reforms when heated to body temperature or when a current is passed through the material via a connected current source. Thus, a catheter (100) manufactured from a shape-memory material, such as nitinol, may be preshaped, for example, in the shape shown in the various shaped catheters herein disclosed, then introduced to the target location for selective mapping and ablation in accordance with the inventive method.

Figure 3:
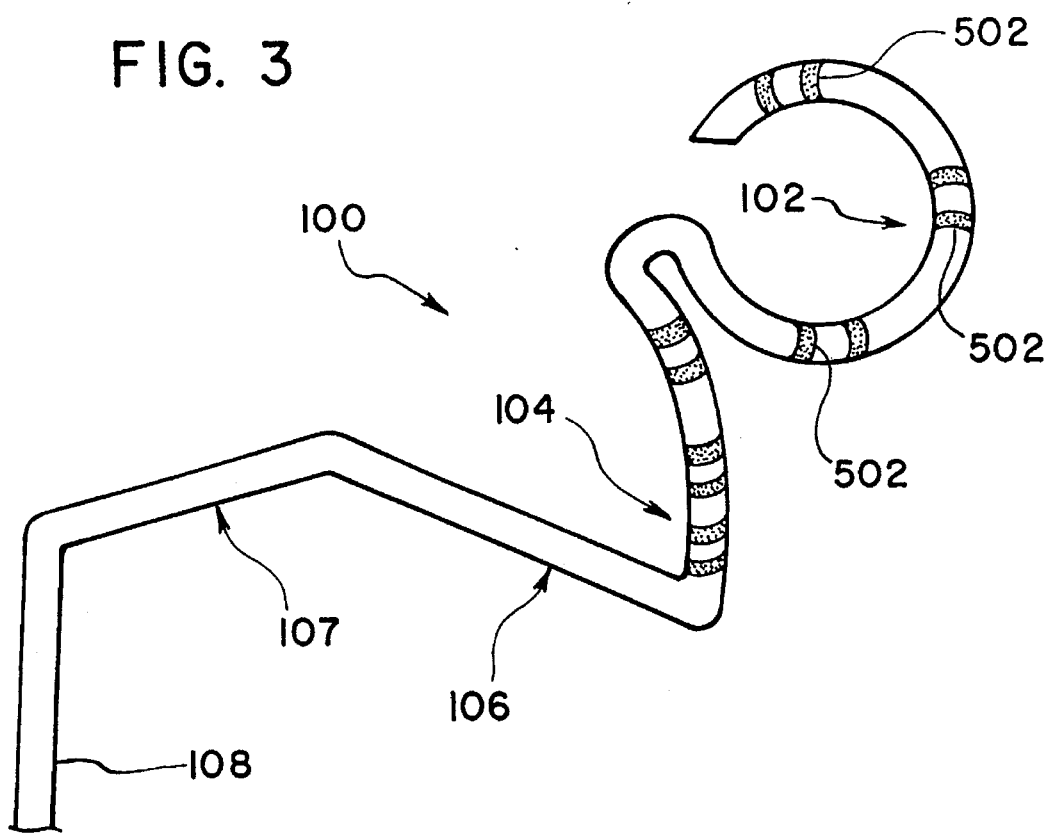
FIG. 3 is a perspective view of an alternative embodiment of a catheter of the present invention.

As illustrated in FIG. 3, the surface of selected portions of the catheter (100) may include one or more electrodes (502) or an array of spaced apart electrodes (502). The electrodes preferably are spaced approximately 2mm apart. Each electrode may be attached to individual respective insulated conductor wires. These wires are threaded through the catheter lumen (113), in the example of a catheter having a lumen (113), or imbedded in the catheter walls (112) if the catheter does not include a lumen (113). The control end of the wires terminate at a control mechanism (not shown). The electrodes (502) preferably are manufactured from platinum tubing, for example such tubing that is about 1–5 mm thick, preferably about 2 mm thick, and about 1–5 mm long, preferably about 4 mm long.

Prior to securing the electrodes (502), each of the electrodes (502) is attached to a respective low resistance conductor wire, that are threaded through small holes in each electrode (502). Each set of conductor wires then may be inserted into a polymer, preferably PTFE, tube that is positioned within the catheter lumen (113). Alternatively, the wires may be embedded within the catheter, either as individual wires or bundled. In some embodiments, the catheter (100) may include a separate lumen for positioning the tube containing the electrode wires out to the electrical control unit (not shown) for the electrodes. Portion 104, depending on the shape, also is in contact with endocardium from portion 102 to the fossa ovalis or to the inferior vena cava.

The electrodes (502) may be used both to map and to ablate target tissue and tissue circuitry in the left or right atrium. The mapping function of the electrodes may be the same as that for many commercially available mapping electrodes. Thus, the electrodes (502) may be connected to a recording system which measures and displays cardiac depolarization potentials sensed within the involved cardiac chamber. The mapping electrodes also may be used together as ablation electrodes. In a preferred embodiment, for ablation of the circuitry effective to treat atrial fibrillation, the electrodes are activated to a current level of between about 40 volts and about 15 volts for a time interval of between about 25 seconds and about 35 seconds. The actual time interval and voltage applied will vary depending on the type of atrial rhythm irregularities being treated and the specific location of the catheter (100), as discussed in further detail below. In an alternative embodiment, the catheter (100) may be used to ablate only, and the mapping function is performed by a separate mapping catheter (100).

One reason for having preshaped catheters of the type described and disclosed herein is to maximize contact of electrodes (502) positioned on the surface of the catheters (100) with the target tissue to improve mapping and selective ablation of the underlying circuitry. In the illustrated embodiment of FIG. 3, the electrodes (502) of the first curved portion (102) are positioned in pairs, each pair being equidistant from each other. However, in the second curved portion (104') of that illustrated embodiment, beginning at the most distal portion, the electrode pairs are a maximum of 4 mm apart. Alternative arrangements of electrodes (502) along the length of the various catheters (100) may be used, depending on the location at which the catheter will be used and the preferred type of lesion to be achieved by the particular catheter.

The catheter (100) shown in FIG. 3 has a pre-formed configuration that is particularly useful in ablating circuitry that causes atrial fibrillation. Specifically, that illustrated catheter (100) includes a first curved portion (102) that is similar to the illustrated catheter (100) of FIG. 1. In a preferred embodiment, the first curved portion (102) is about 1.5–2.5 cm in diameter. The illustrated catheter (100) is preshaped such that the first curved portion (102) of the catheter fits in contact with the endocardium posterior and inferior of the ostium of the coronary sinus. The illustrated catheter (100) also includes a second (104), a third (106), and a fourth portion (107) contiguous with the shaft (108) that assist in securing the first curved portion (102) in its position around the os (200).

Figure 4A:
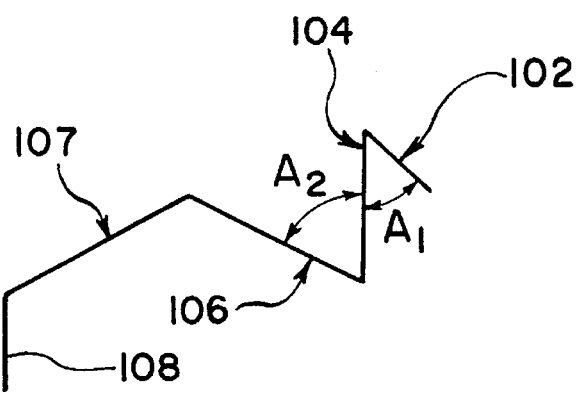
FIGS. 4A and 4B are representations of the catheter of FIG. 3 in a first, pre-positioned configuration (FIG. 4A) and a second, positioned configuration (FIG. 4B).
Figure 4B:
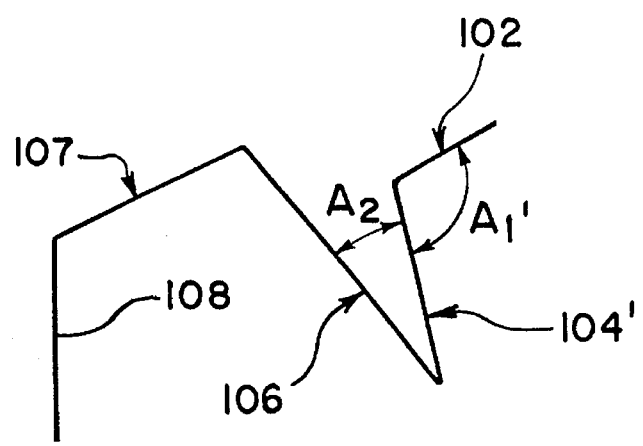

Turning now to FIGS. 4A–4B, those schematically illustrate the change between the pre-position configuration (at FIG. 4A) and the positioned configuration (at FIG. 4B) of the catheter illustrated in FIG. 3. As shown, the angle ($A_1$) between the first curved portion (102) and the second curved portion (104'), changes to a more obtuse angle $A_1'$ when it is positioned at the ostium (200) and as the second curved portion (104') slides forward to become flush against the endocardium. As the third portion (106) slides forward to support the second curved portion (104') and to maintain the height of the first curved portion (102), the angle (A₂) between the second curved portion (104') and the third portion (106) becomes more acute once the catheter (100) is in position. The first curved portion (102) may be limited in its motion by a pre-inserted catheter at the ablation site for recording circuit activity in the ablation area.

Figure 5:
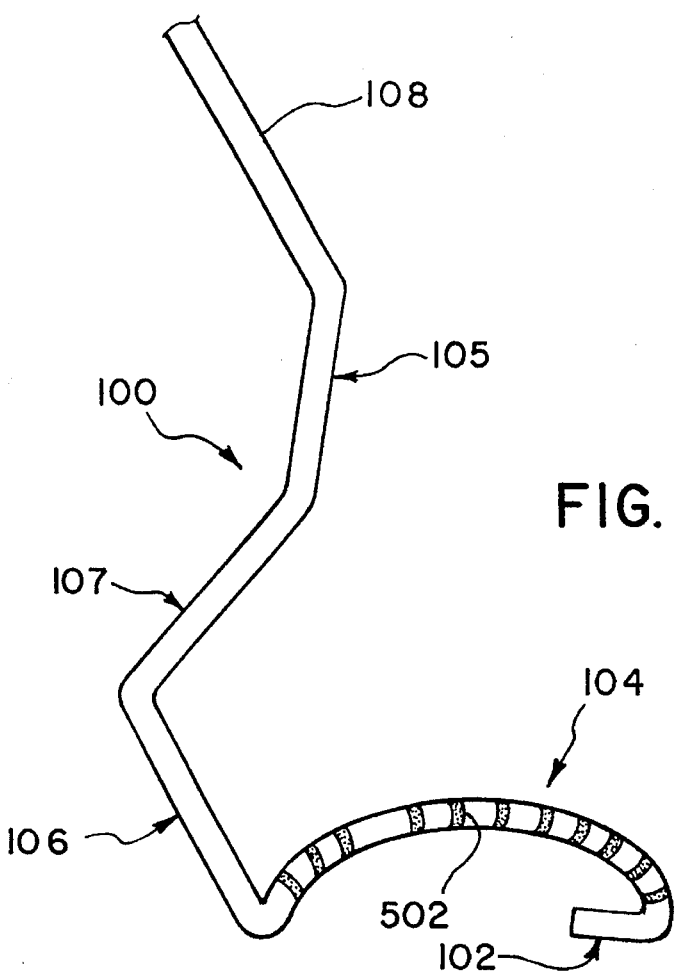
FIG. 5 is an alternative embodiment of a catheter of the present invention.

The catheter (100) of the present invention may be configured for a variety of mapping and ablation functions, depending on the intended treatment. As such, the specific shape of the catheter (100) may change. The catheter (100) illustrated in FIG. 5 is one example of an alternative catheter (100) configuration, shown in its pre-shaped form. In that illustrated embodiment, the catheter (100) is designed for use with curvilinear lesions. The illustrated catheter (100) includes an additional portion (105) both between and contiguous with the fourth (107) portion and the shaft (108). The illustrated catheter (100) includes spaced apart electrodes (502). In an alternative embodiment, the catheter may include electrode pairs, or that includes electrodes (502) spaced apart at intervals different from those illustrated.

Figure 6:
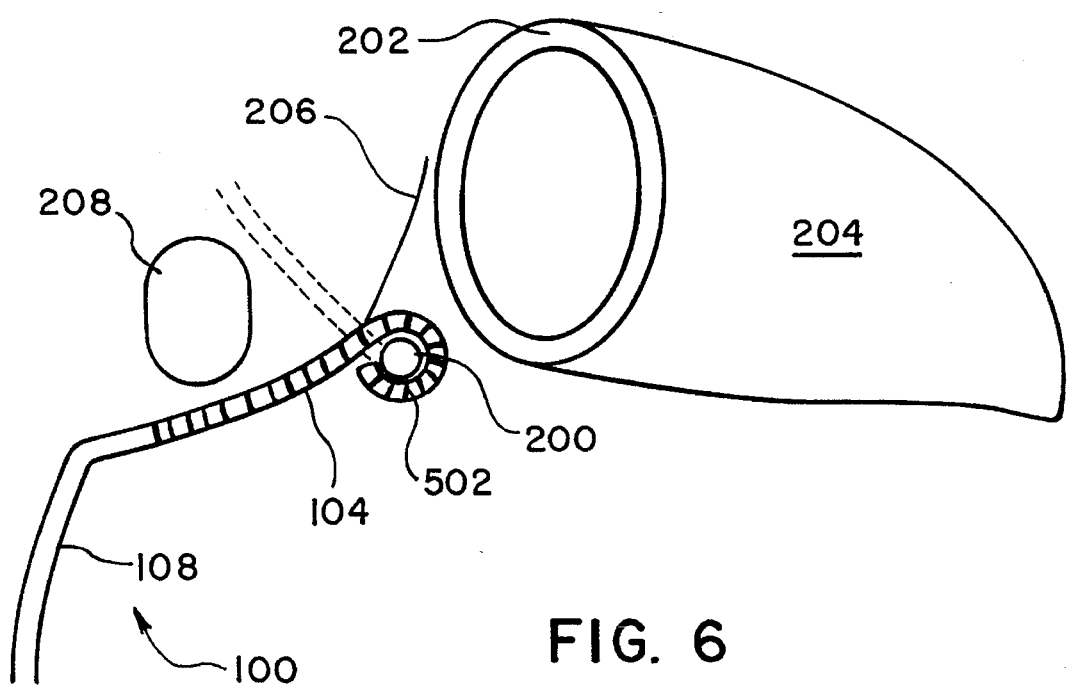
FIG. 6 is a perspective view of the catheter of FIG. 1 positioned around the ostium of the coronary sinus.

In a preferred method of practicing the present invention, an embodiment of the catheter (100) having the guide-wire (110) therein is used. The catheter (100) is advanced toward the coronary sinus through a great vein, such as the femoral vein. The catheter (100) is advanced through the inferior vena cava until the tip ( 111 ) of the guide-wire rests across the tricuspid valve (202) of the right ventricle (204). The catheter (100) then may be benched, and the guide-wire (110) withdrawn. As the guide-wire (110) is withdrawn, the catheter (100) assumes its preshaped form, for example the shape shown in FIG. 1, and curves around the ostium of coronary sinus (200). A catheter (100) thus positioned is shown in FIG. 6. Note the position of the catheter (100) in FIG. 6 relation to the fossa ovalis (208) and the tendon of Todaro (206) between which the second curved portion (104) is positioned. In that position, the second curved portion (104) secures the first curved portion (102) containing the electrodes (502) in place around the os (200).

Figure 7:
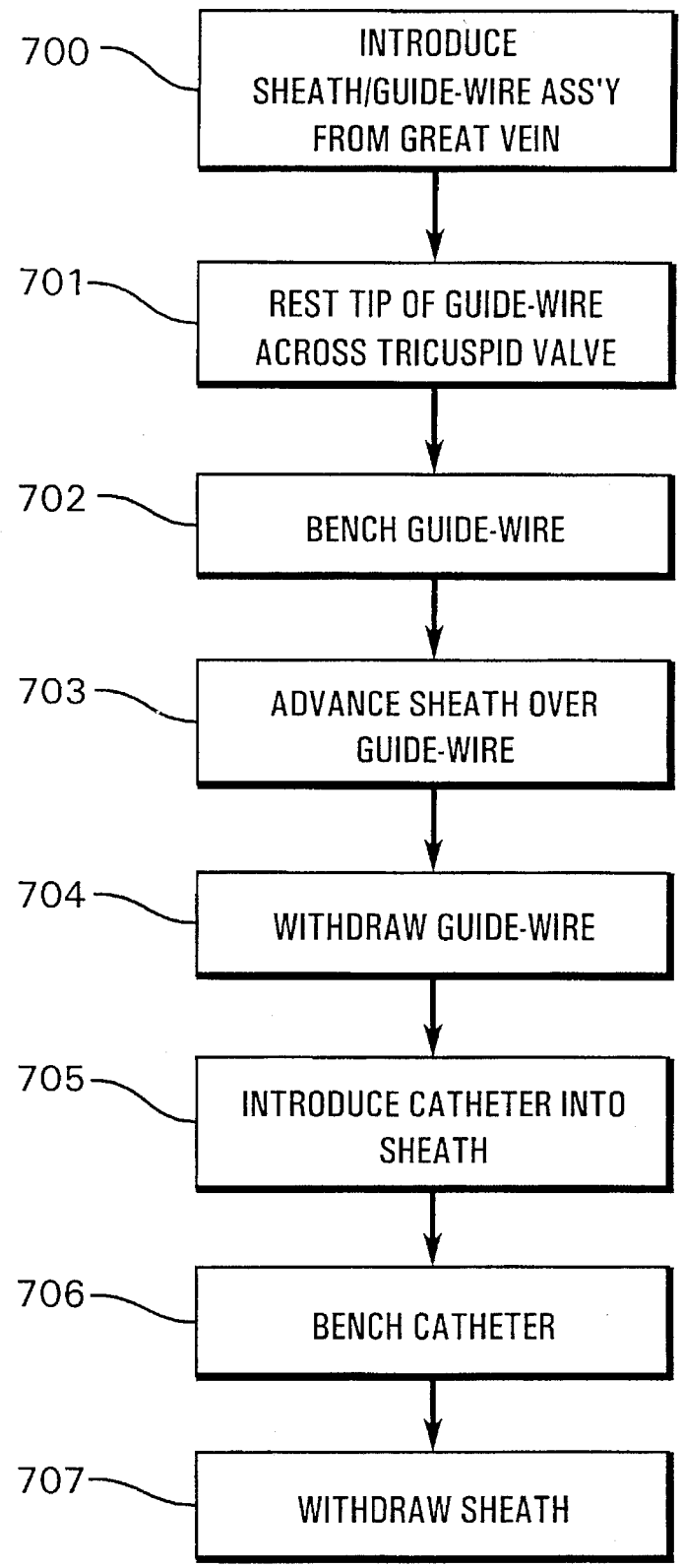
FIG. 7 is a flowchart demonstrating use of the sheath/guide-wire catheter assembly of FIG. 2C.

In using the guide-wire/sheath assembly (120) shown in cross-section in FIG. 2C, the guide-wire (110) is assembled within the sheath (300) prior to introduction of the assembly (120) into any of the structures. An exemplary method of positioning the catheter (100) around the ostium (200) using such a guide-wire/sheath assembly (120) of the present invention is outlined in the flowchart of FIG. 7. The assembly (120) is introduced (700) through a great vein, such as the femoral vein. Once the tip (111) of the guide-wire rests (701) across the tricuspid valve (202), the guide-wire (110) may be benched (702) and the sheath (300) advanced (703) over the guide-wire (110) until the sheath (300) rests at the entrance of the atrioventricular junction of the right ventricle. The guide-wire (110) then is withdrawn (704) and the sheath left in position. The catheter (100) next is introduced (705) into the vascular sheath (300) until the catheter (100) reaches the distal tip of the sheath (300). The catheter (100) then is benched (706) and the sheath (300) withdrawn (707), leaving the preshaped catheter (100) in place around the ostium of coronary sinus (200), as shown in FIG. 6.

The present catheter (100) may be used in conjunction with a plurality of other shaped catheters. Also, each of the shaped catheters (100) herein disclosed may be used alone, or in various combinations to achieve the desired ablation. The exact shape of each catheter depends on the specific application for that catheter, as shown in the figures incorporated herewith. Each catheter (100) includes a first (102) and a second (104) curved portion, which second curved portion (104) functions to retain the first curved portion in its desired position within the atrium.

FIGS. 8A–8C illustrate alternative exemplary catheters (100) that may be used for endocardial mapping and linear lesions. In a preferred embodiment, each electrode (502) is 2 mm wide; however, in other embodiments the electrodes may be between about 1–6 mm wide and spaced apart as described above. FIG. 8A illustrates the catheter (100) with a straight tip portion (101). FIG. 8B shows a more detailed depiction of the top portion of the catheter, including the array of spaced apart electrodes (502).

As shown in FIG. 8A, the first curved portion (102) of the catheter is only slightly curved, whereas the second (104) and third (106) curved portions are close together and relatively more curved. The first portion (102) through the second portion (104) of the catheter (100) is in contact with the endocardium. As shown, the catheter (100) is angled such that the lower portions from the third curved portion (106) through the end of the catheter (108) are not in contact with the endocardium. Whereas most angioplastic catheters are designed into a two-planed geometry, the illustrated catheter is angled back at approximately a 90° angle to secure the catheter in the desired position against the endocardium.

As exemplified in the embodiment illustrated in FIG. 8C, the curved portion between the portions (104) and (106) may form a notch (800) designed to fit by the side of the mitral annulus or the valve ring, particularly when the catheter (100) is introduced from the aorta. The notch thus functions to hold the portion of the catheter having the electrodes in place against the endocardium for accurate and complete ablation of the area under that catheter. The illustrated catheter of FIGS. 8A–8C may be introduced into the right atrium (203) via either the superior vena cava (210) or the inferior vena cava (212), depending on the target ablation area.

Figure 9B:
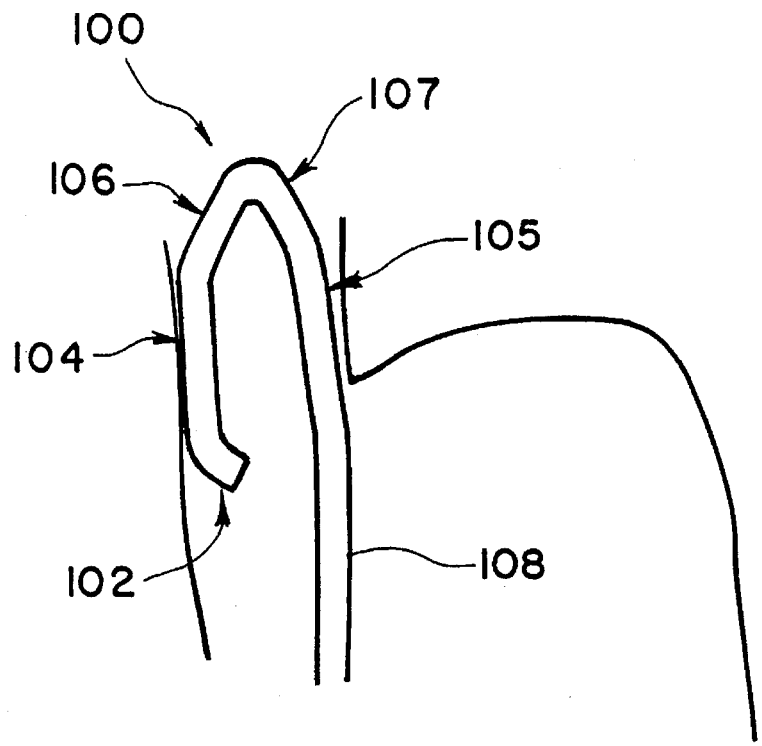
FIG. 9B shows that embodiment in position in the right atrium and superior vena cava.
Figure 9C:
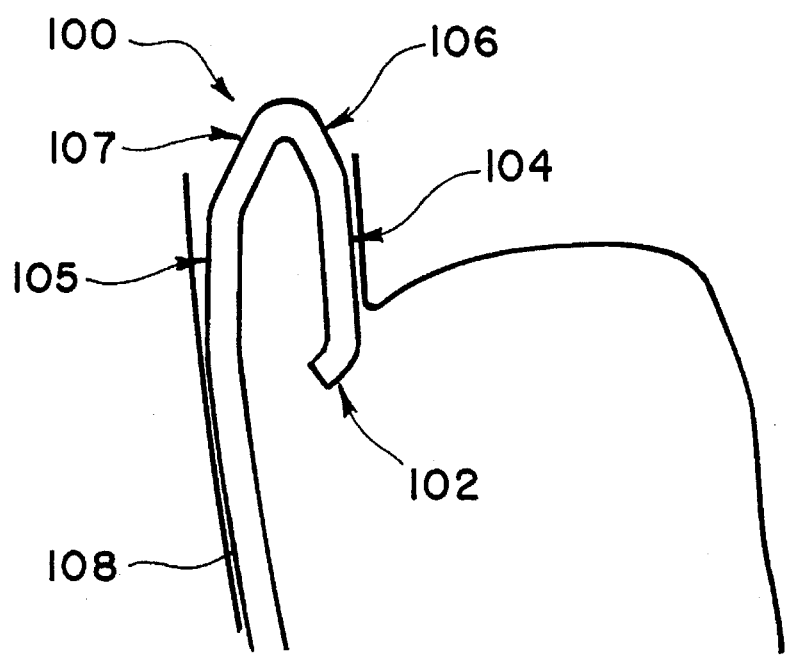
FIG. 9C shows that embodiment in an alternative position in the right atrium and superior vena cava.

FIG. 9A shows yet another exemplary catheter (100) of the present invention, in its shaped form. That illustrated embodiment is particularly useful for ablating the region of the sinoatrial node, the left atrium and left atrial side of the ostium of coronary sinus (200) and the surrounding area extending up to the mitral valve (220) in FIG. 16. Catheter stability and contact with the wall of the atrium (203) is enhanced by a tension that exists by design between the third curved section (106) and a fourth (107) and fifth (105) curved sections. FIGS. 9B–9C show an exemplary use of the illustrated catheter (100) of FIG. 9A. Preferably, the catheter (100) is introduced via the inferior vena cava (212) such that it extends up partially into the superior vena cava (210). Once in position, the catheter (100) shape is invoked, either by withdrawing a guide-wire (110) contained therein, or by passage of electrical current or warming if the catheter (100) is manufactured by a temperature-sensitive shape memory material, such as nitinol.

Description of the Methodologies

In treating abnormal cardiac rhythms, such as atrial fibrillation, specific cardiac circuitry is ablated using the catheters of the present invention. Typically, the circuitry in both the left atrium and right atrium should be disrupted to effectively treat atrial fibrillation, though such requirements may not apply to treatment of other abnormal cardiac rhythms.

Figure 10A:
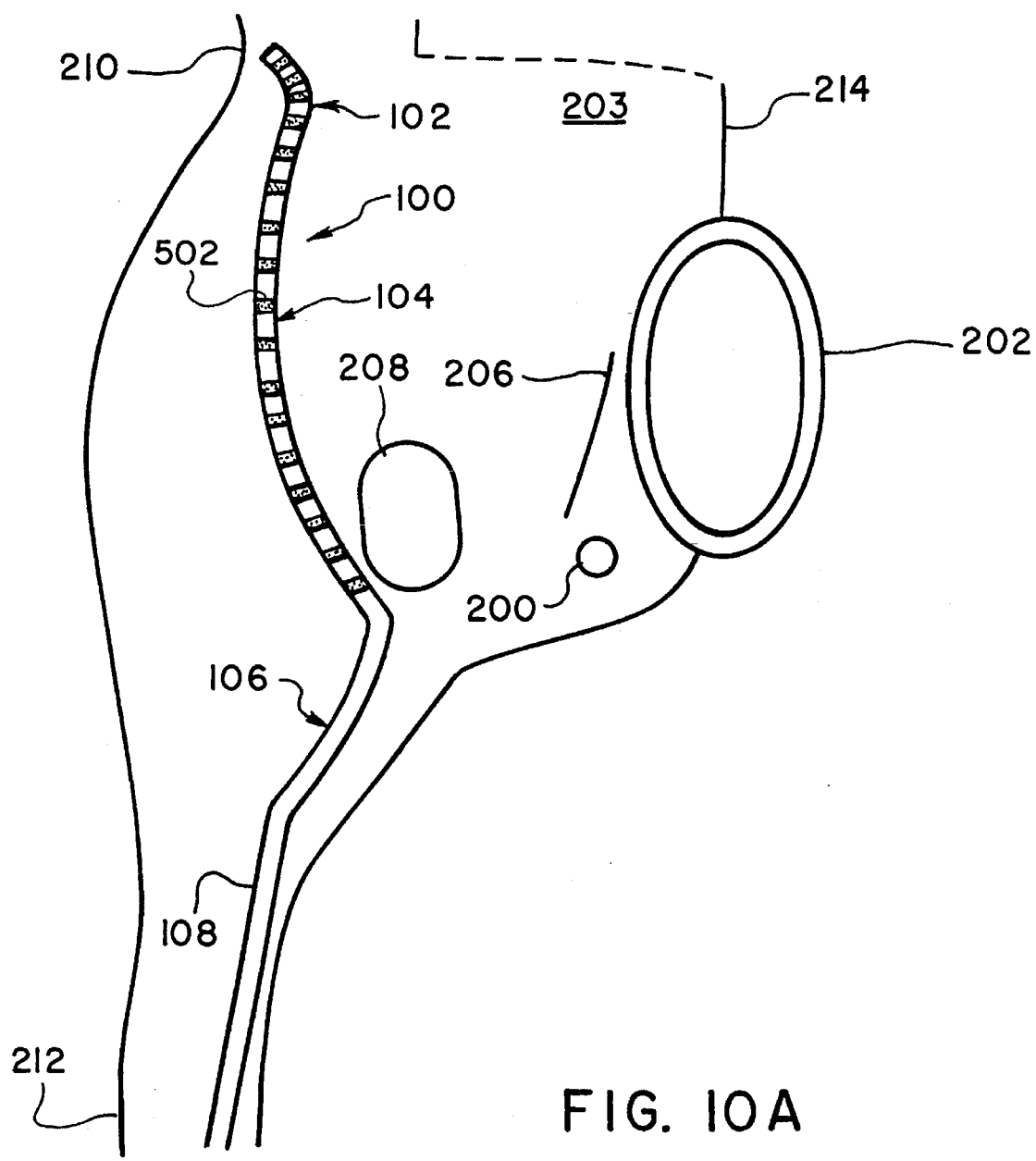
FIGS. 10A–10C show the embodiment of FIGS. 8A–8B in alternative positions in the right atrium via the inferior vena cava.
Figure 10B:
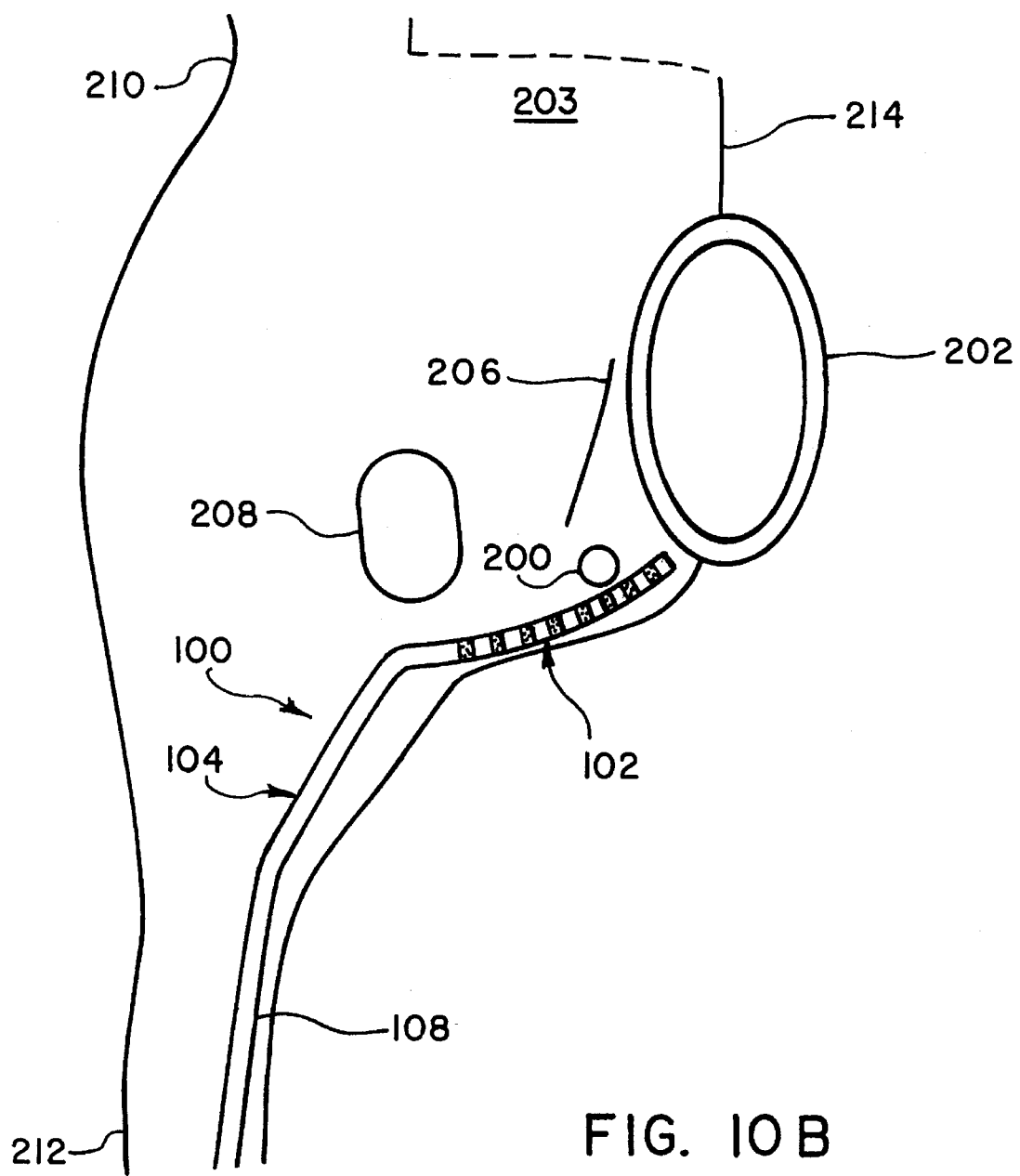
Figure 10C:
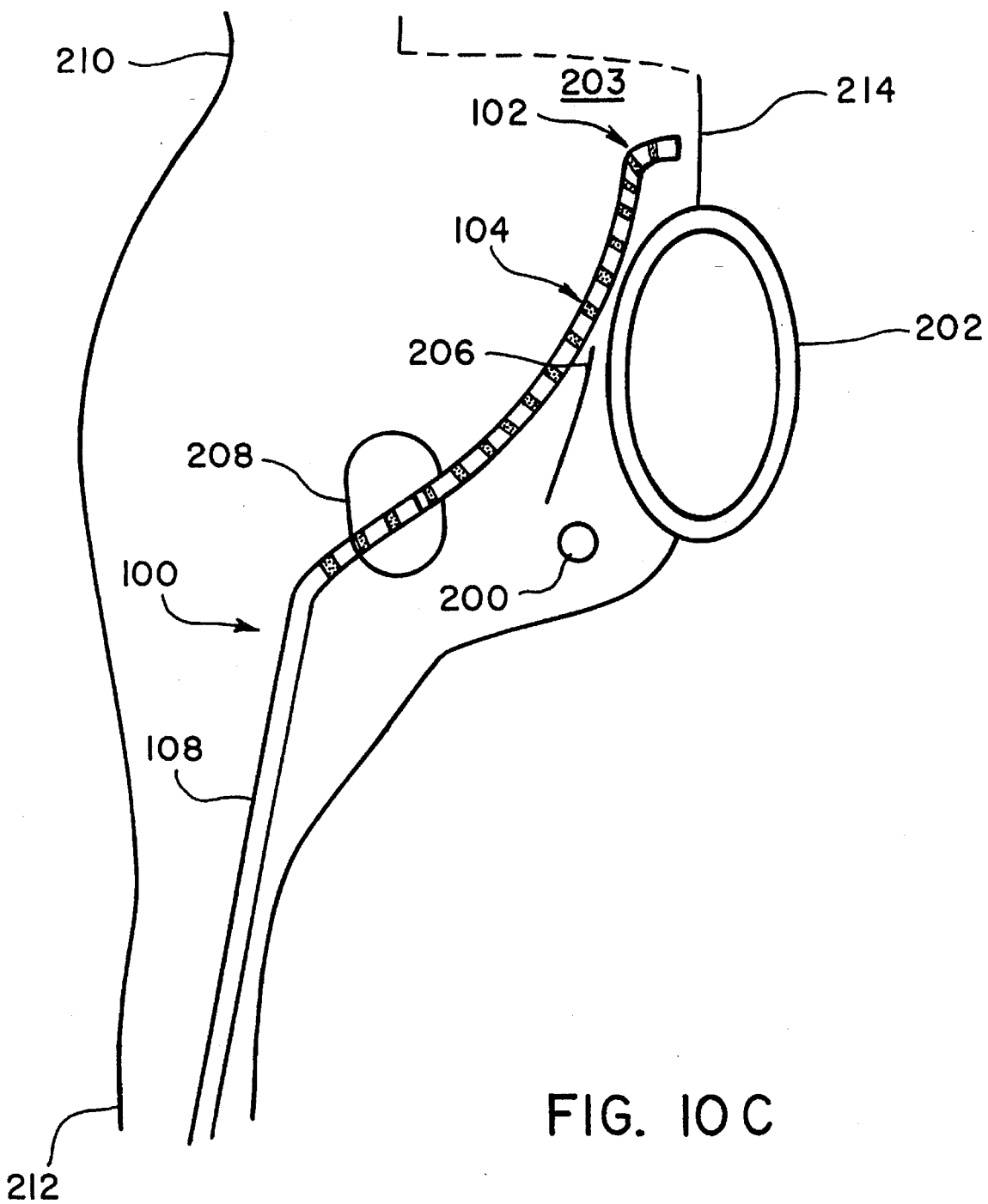
Figure 11:
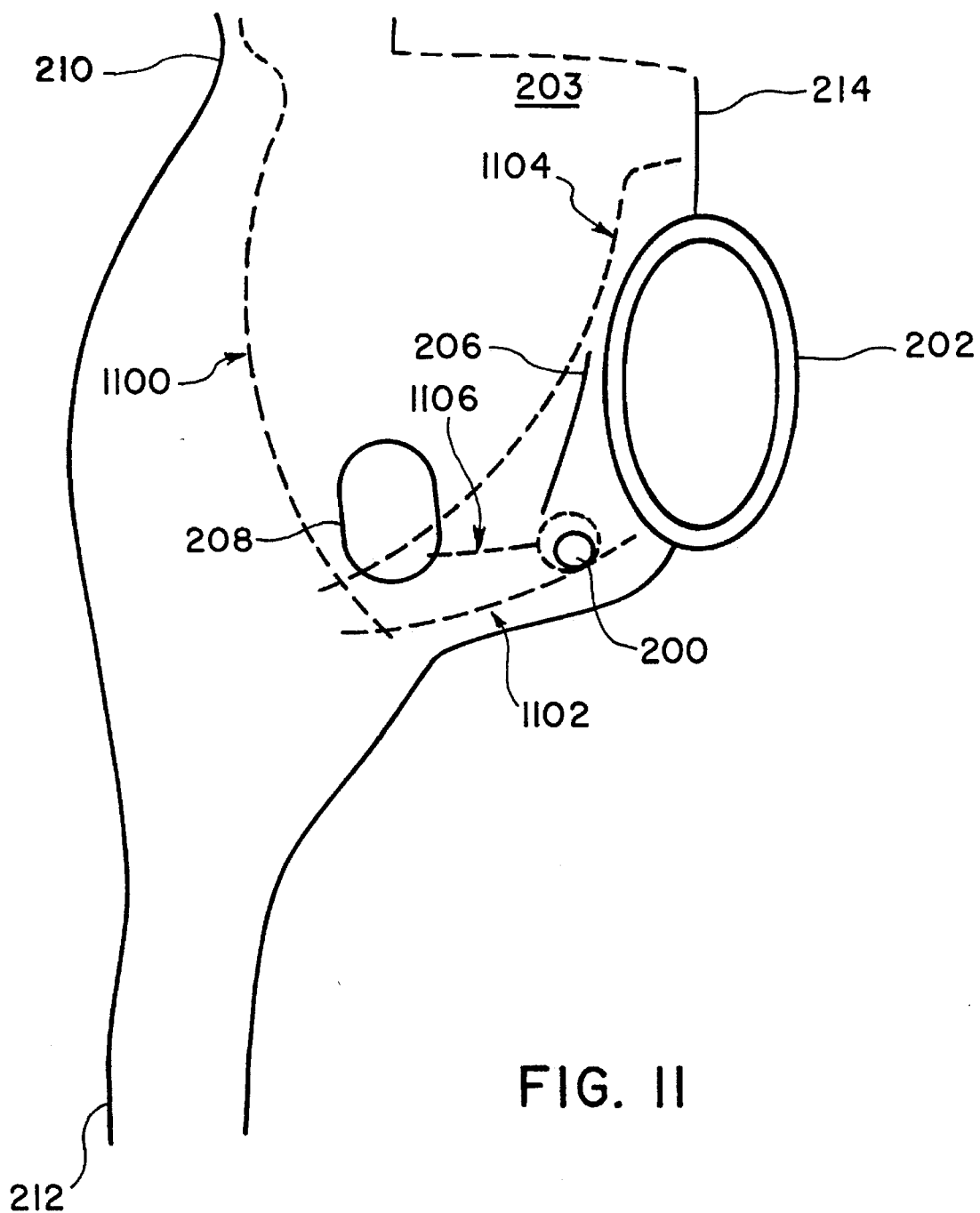
FIG. 11 illustrates a summary of ablation lesions that may be produced using multiple positions of the catheter as illustrated in FIGS. 10A–10C and the catheter of FIG. 3 in position around the ostium of the coronary sinus.
Figure 17:
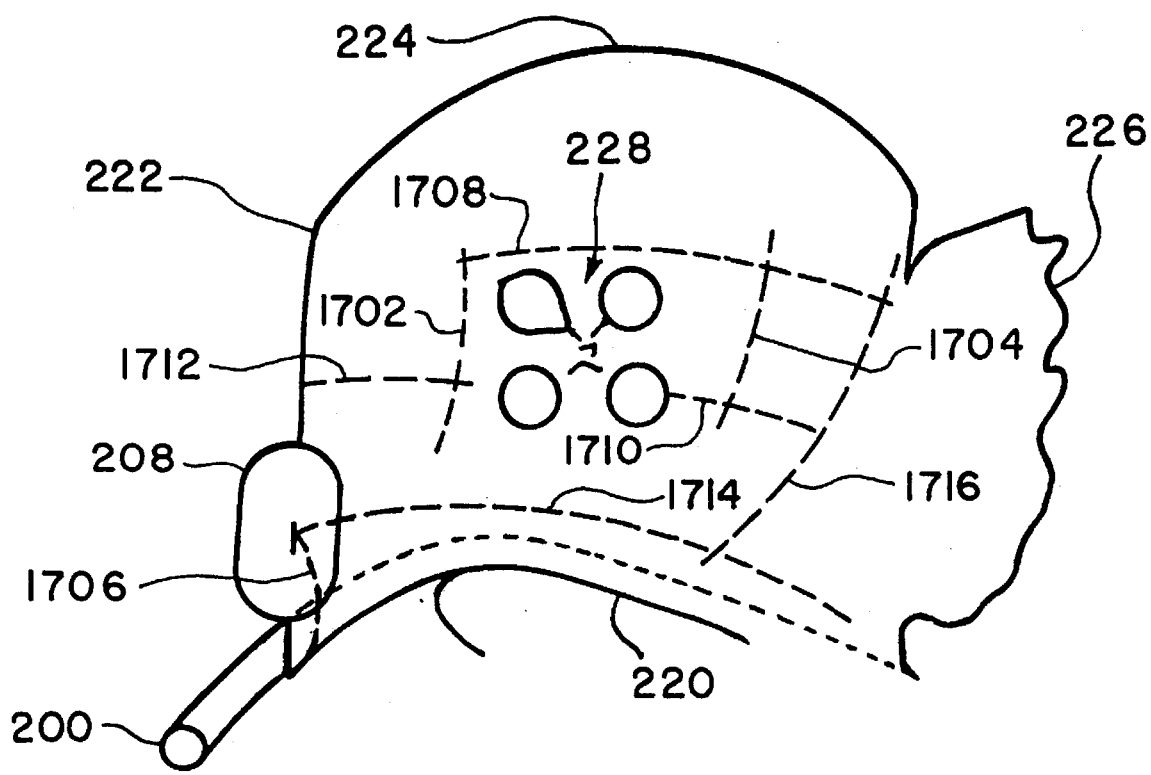
FIG. 17 shows a summary of lesions that may be produced using a combination of the catheter positions shown in FIGS. 16A–16H.

FIGS. 10A–10C show a catheter in alternative positions in the right atrium. The ablation pattern made by application of electric current through the electrodes (502) positioned on the first (102) or second curved portion (104) of the catheters shown in FIGS. 10A–10C and FIG. 6 (with second curved portion 104 positioned accross the os (200) of the coronary sinus) is illustrated in FIG. 11. This ablation pattern, together with the ablation pattern as shown in FIG. 17 in the left atrium, results in the disruption of circuitry sufficient to treat atrial fibrillation. The atrial circuitry beneath the electrodes (502) positioned on the first curved portion (102) of the catheter (100) which is positioned as shown in FIG. 10A is illustrated by ablation line (1100). The atrial circuitry beneath the electrodes (502) positioned on the first curved portion (102) of the catheter (100) which is positioned as shown in FIG. 10B is illustrated by ablation line (1102) in FIG. 11. The atrial circuitry beneath the electrodes (502) positioned on the first (102) and second (104) curved portions of the catheter (100) which is positioned as shown in FIG. 10C is illustrated by ablation line (1104) in FIG. 11 Finally, the atrial circuitry beneath the electrodes (502) positioned on the first (102) and second (104) curved portions of the catheter (100) which is positioned as shown in FIG. 6 is illustrated by ablation line (1106) in FIG. 11 In FIGS. 10A through 10C, the catheter (100) is introduced into the right atrium (203) via the inferior vena cava (212) to ablate tissue at preselected locations in the right atrium (203).

Figure 12A:
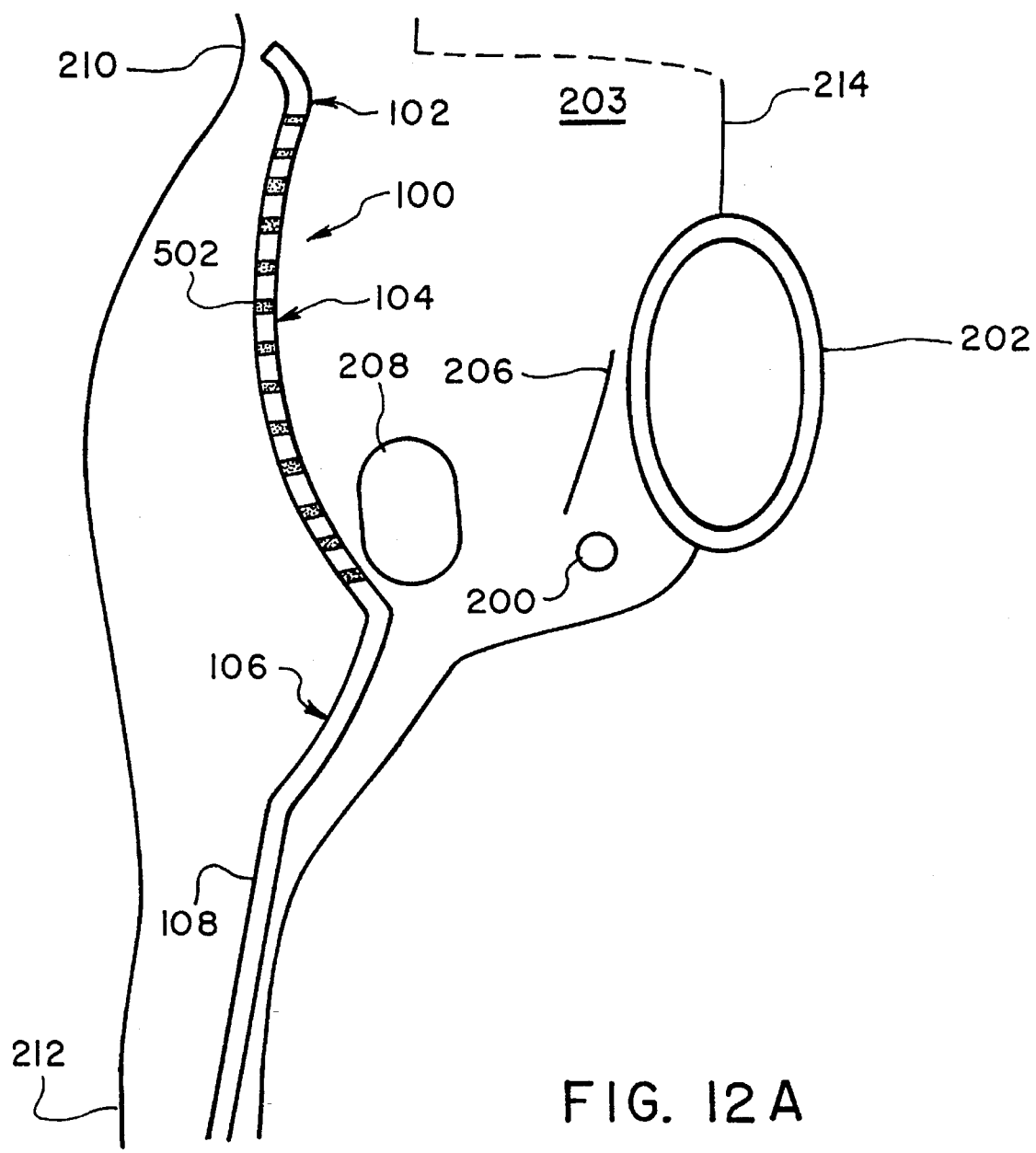
FIGS. 12A and 12C show the embodiment of FIGS. 8A–8B in alternative positions in the right atrium via the inferior vena cava.
Figure 12B:
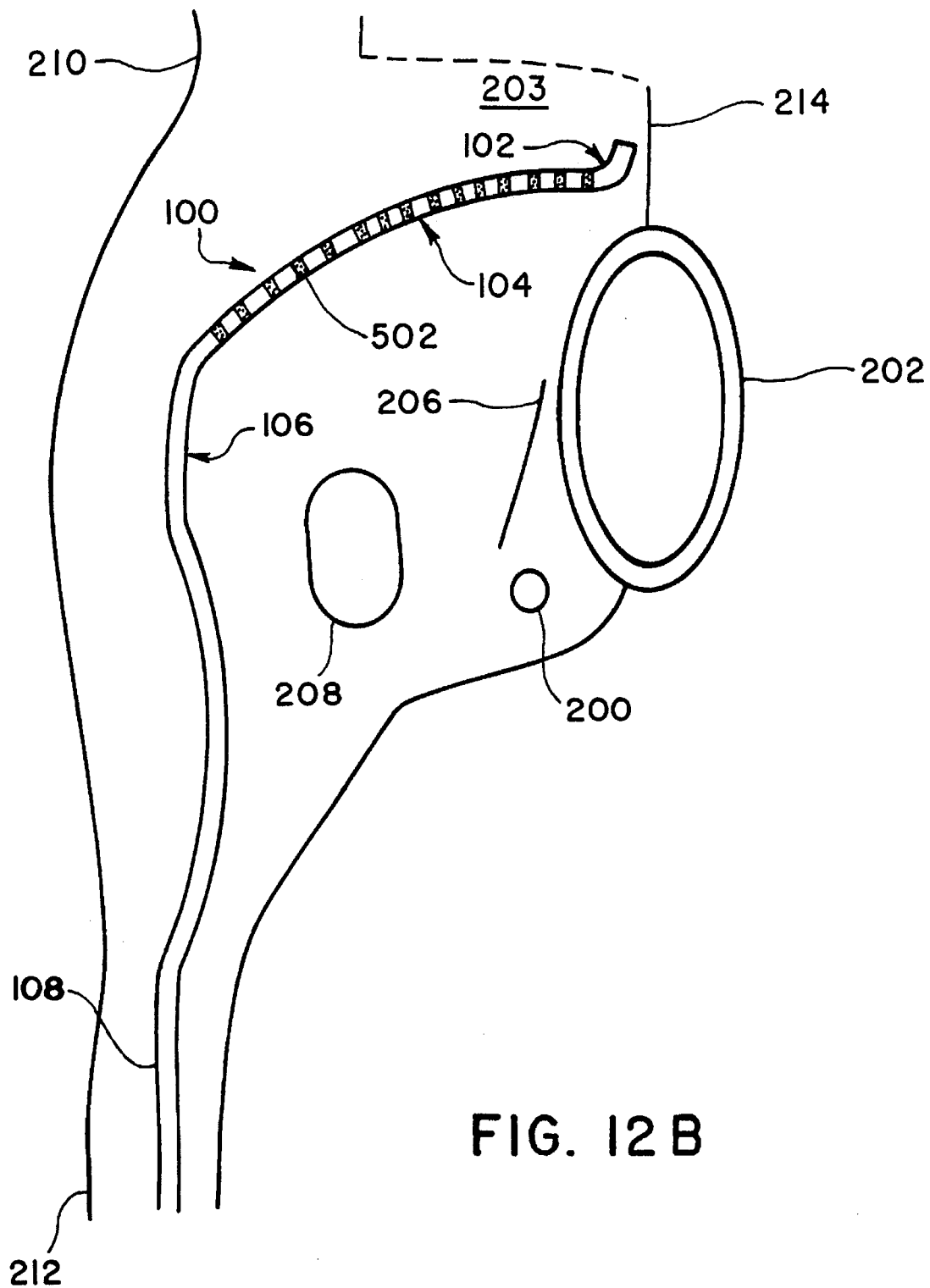
FIG. 12B shows the embodiment of FIG. 5 in position in the right atrium via the inferior vena cava.
Figure 12C:
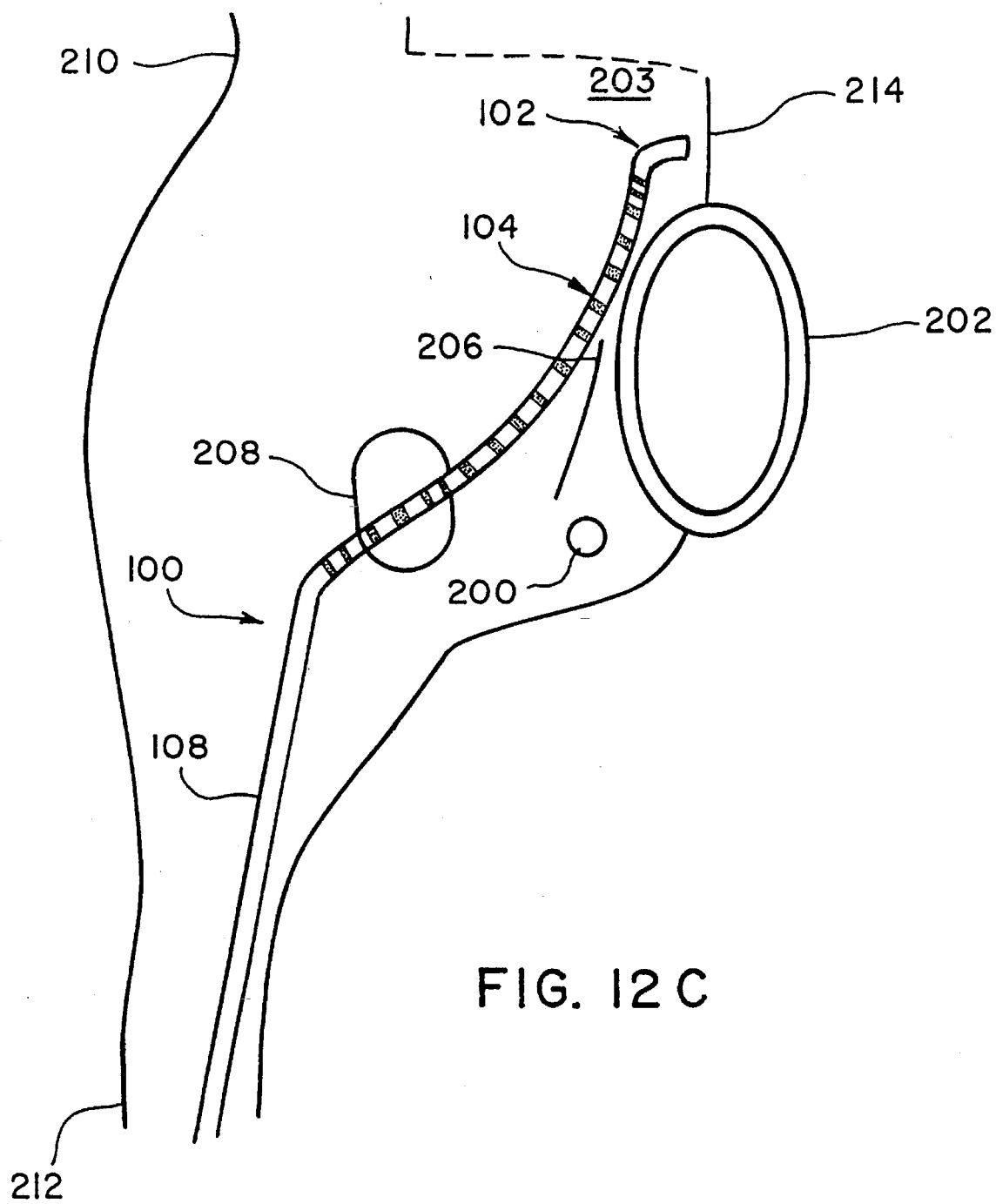
Figure 12D:
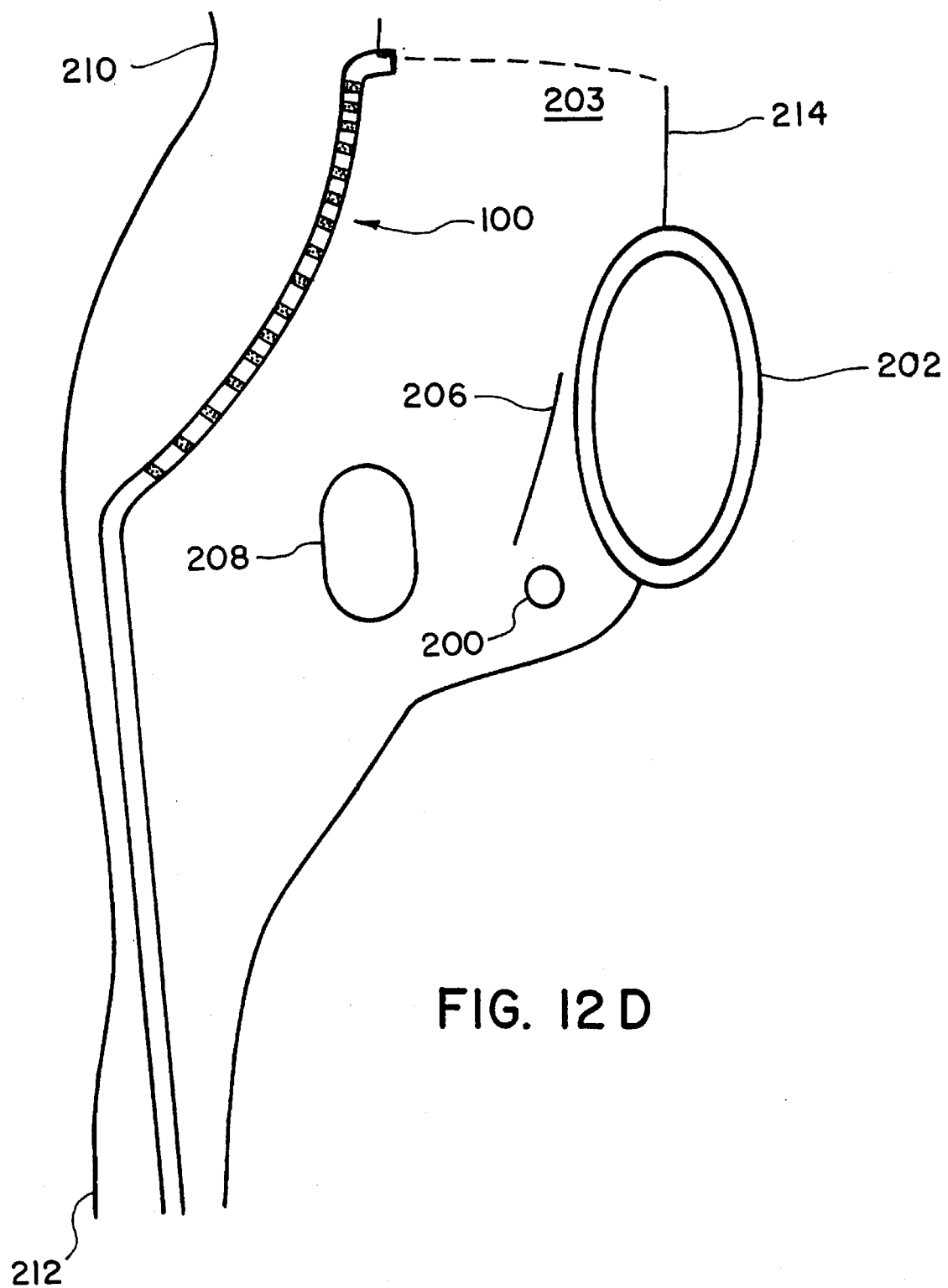
FIG. 12D shows an alternative placement of the catheter of FIG. 8B.
Figure 13:
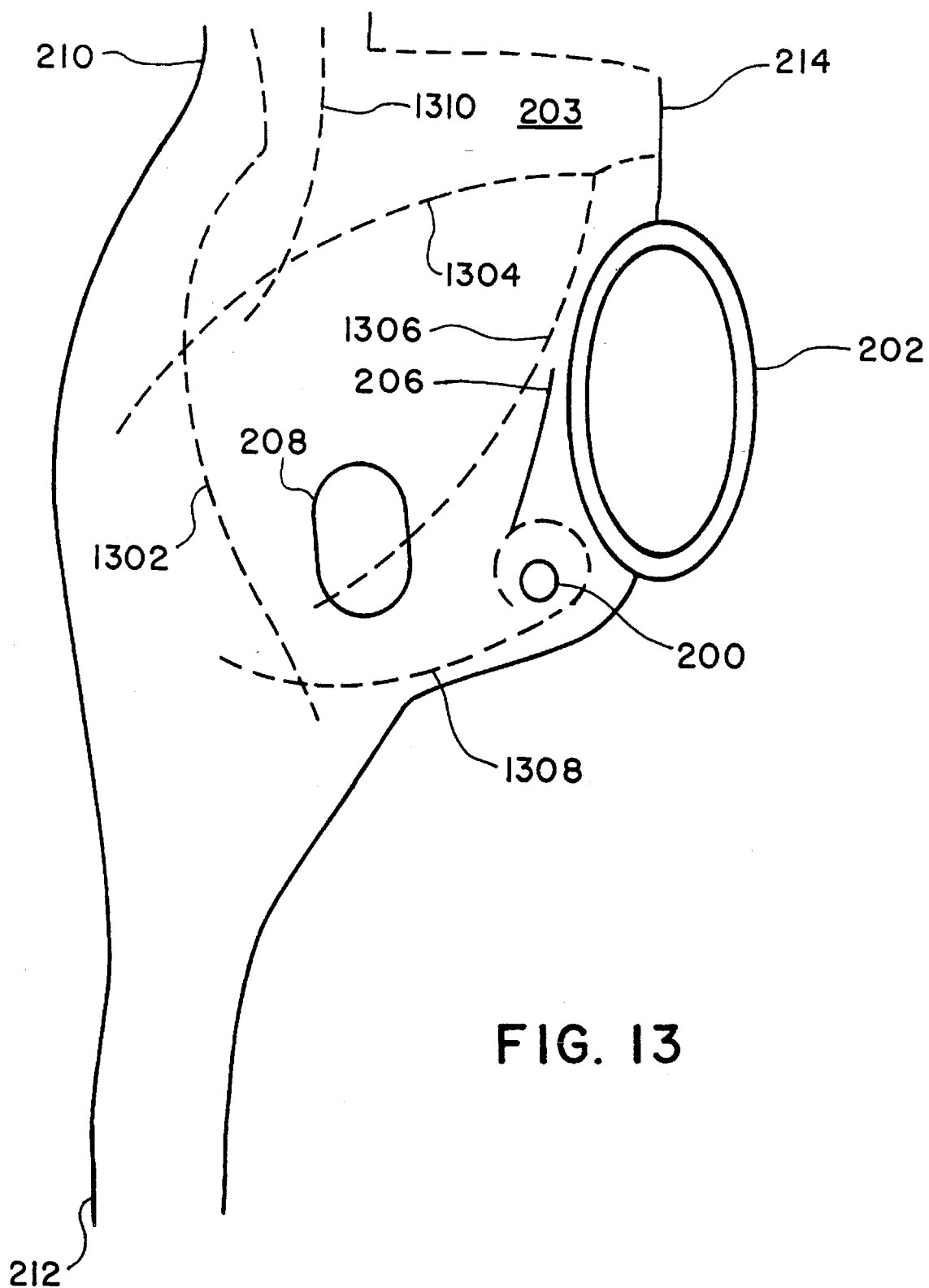
FIG. 13 illustrates a summary of ablation lesions that may be produced using multiple positions of the catheter as illustrated in FIGS. 12A–12C and in FIG. 3.

FIGS. 12A–12C illustrate an alternative pattern and method for ablating atrial circuitry useful in treating atrial fibrillation. The ablation pattern resulting from the positioning of a catheter (100) as shown in FIGS. 12A–12C and in FIG. 6, is illustrated in FIG. 13. In that FIG. 13, the ablation line (1302) is created by positioning the catheter (100) as shown in FIG. 12A, the ablation line (1304) is created by positioning the catheter (100) as shown in FIG. 12B, the ablation line (1306) is created by positioning the catheter (100) as shown in FIG. 12C, and the ablation line (1308) is created by positioning the catheter (100) essentially as shown in FIG. 6. An additional ablation line (1310) may be created by positioning a catheter (100) through the inferior vena cava (212) as shown in FIG. 12D.

The ablation patterns illustrated in FIGS. 11, 13, and 17 are intended to ablate the medial, right anterior, posterior, and left atrial inputs of the atrioventricular node. Since atrial fibrillation is a result of four inputs of the atrioventricular node, the left atrial, medial, right anterior, posterior and disorderly communication between the four in humans. A catheter (100) that is introduced into the right atrium (203), either as illustrated in FIGS. 11 and 13 and left atrium as in FIG. 17, or otherwise, are sufficient to disrupt these important circuit pathways. Note that the catheter of FIG. 3 covers three of six necessary sites when wrapped around the ostium of the coronary sinus (200).

In alternative embodiments, the lesion patterns shown in FIGS. 11 and 13 may be achieved by approaching the atrium with the illustrated catheters (100) via the superior vena cava instead of through the inferior vena cava as shown. It also may be possible to achieve such illustrated lesion patterns by introducing catheters (100) into the atrium via a combination of the superior and inferior vena cava, depending on the desired surgical approach, or the physical condition of the various passageways.

The catheters (100) illustrated above are primarily introduced into the right atrium (203) via the inferior vena cava (212). However, as shown in FIGS. 14A through 14G, the atrial circuitry also may be ablated by positioning the catheters (100) through the superior vena cava (210). The ablation pattern made by application of each of these catheters in the illustrated positions is shown in FIG. 15.

Figure 14A:
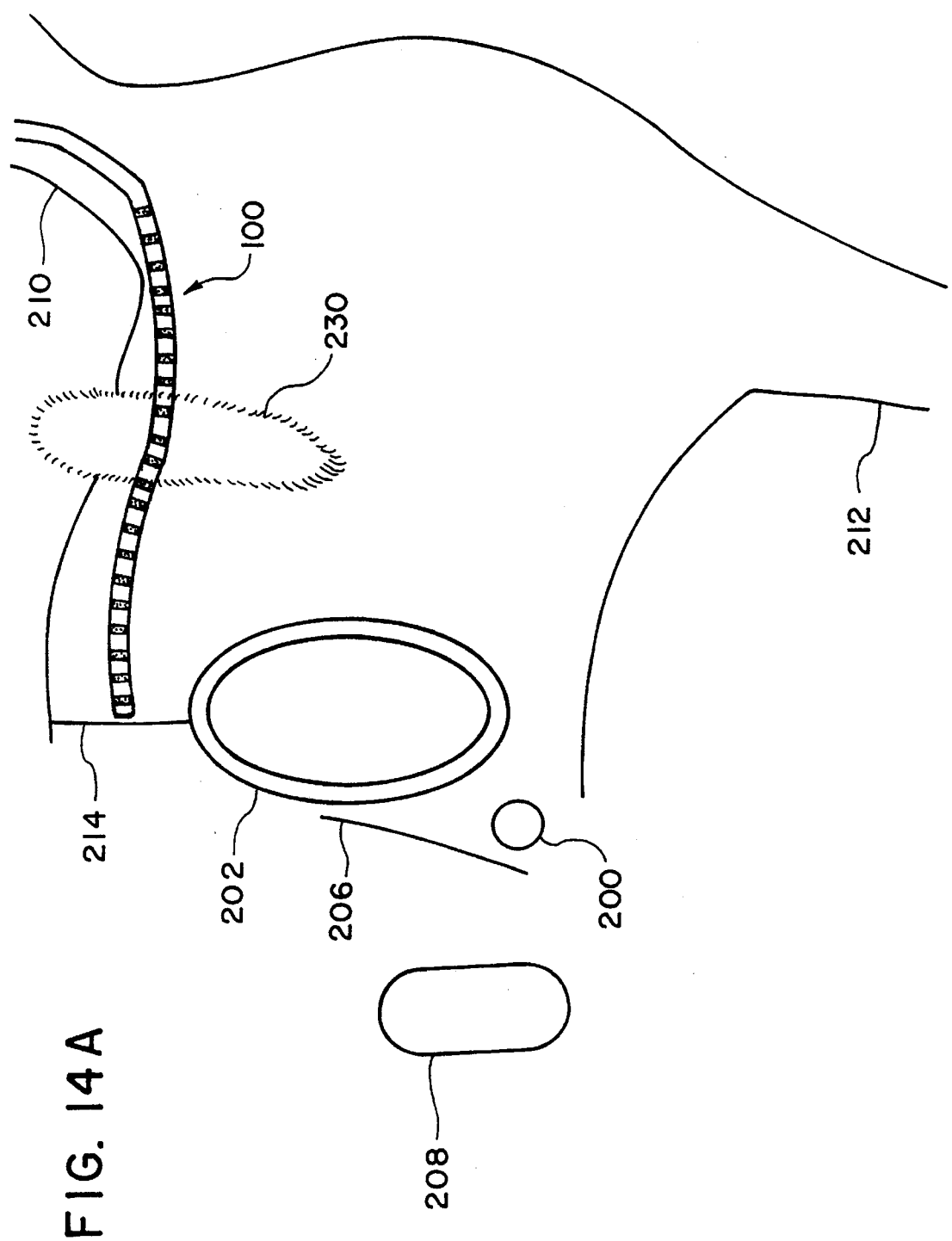
Figure 14B:
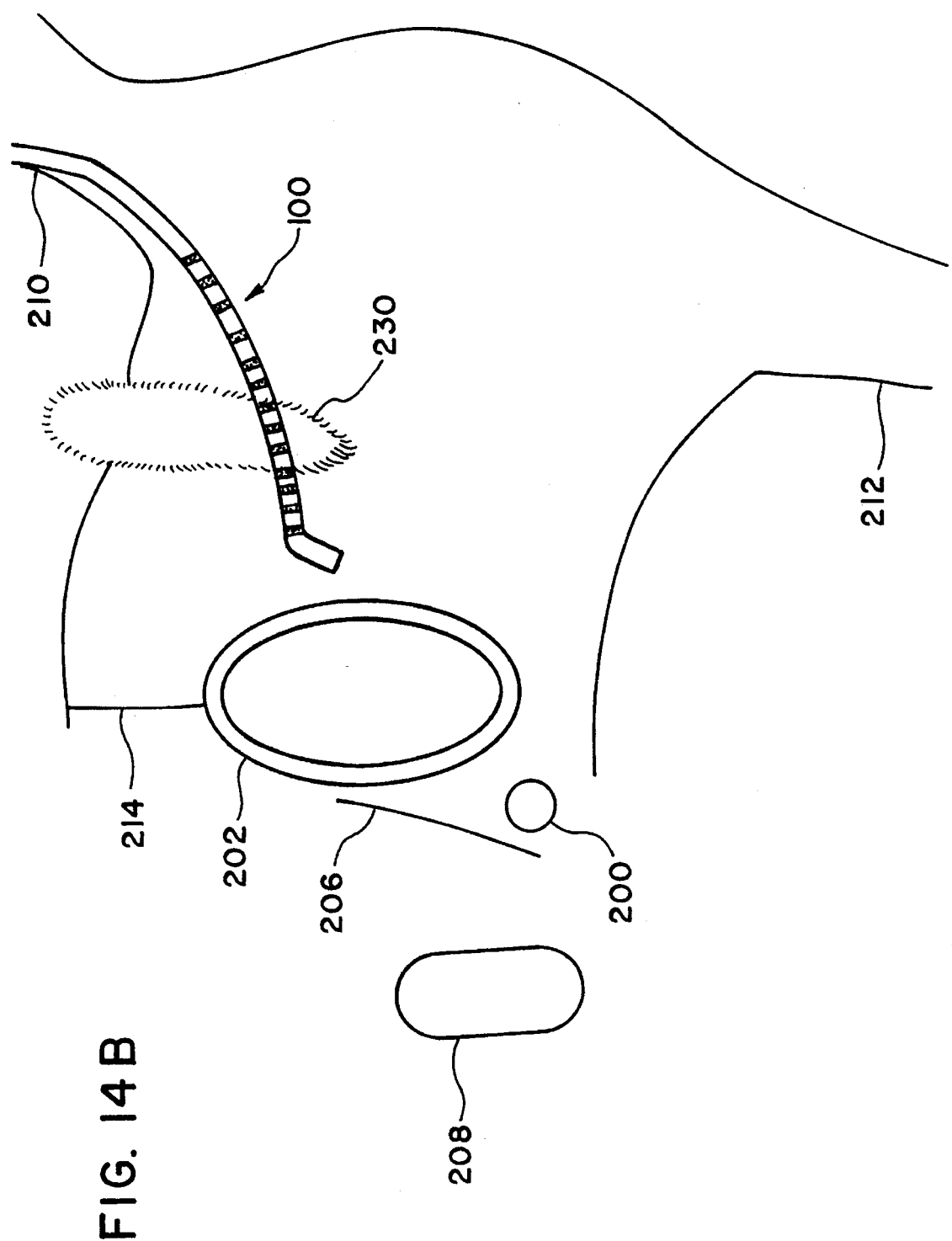
Figure 14C:
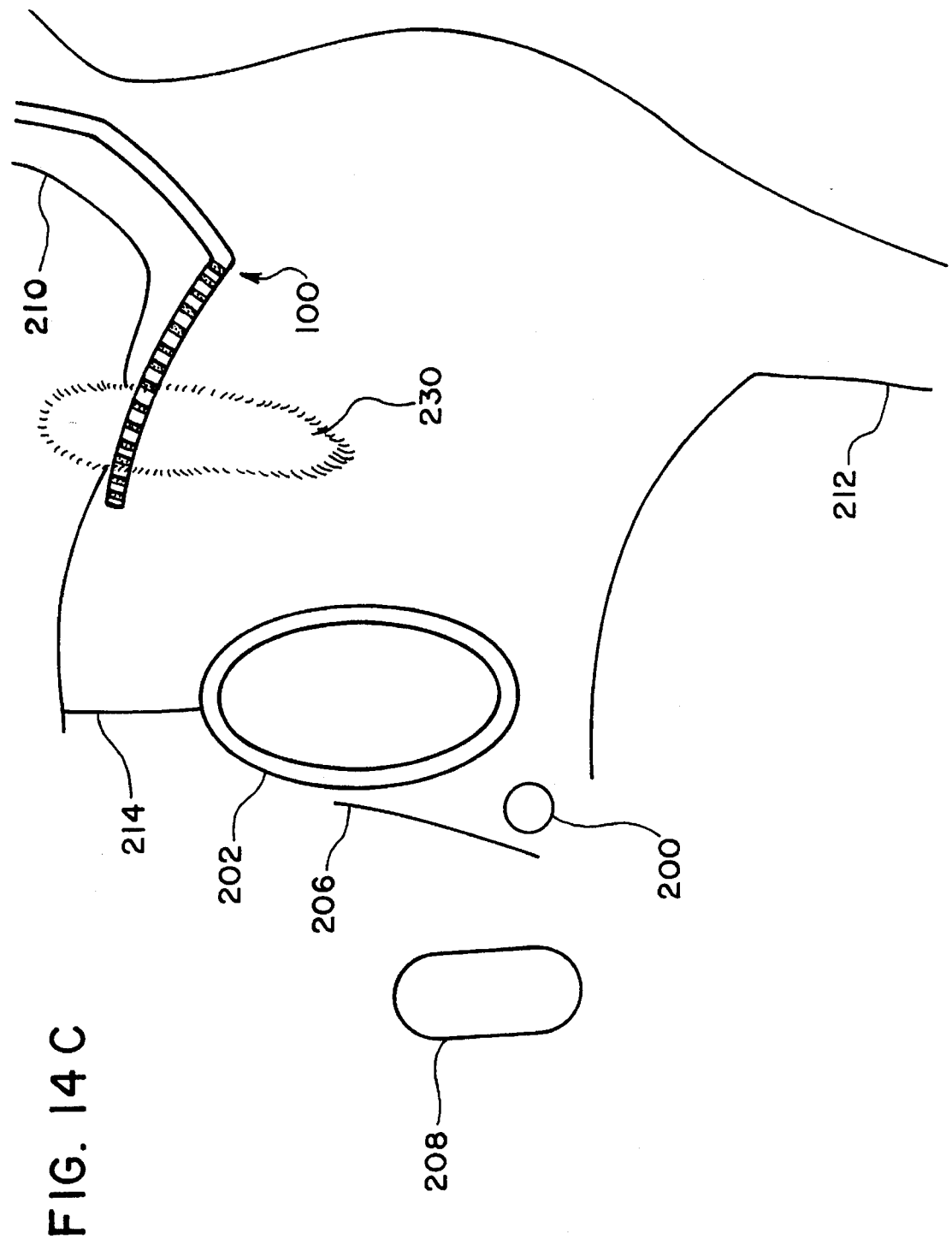
Figure 14E:
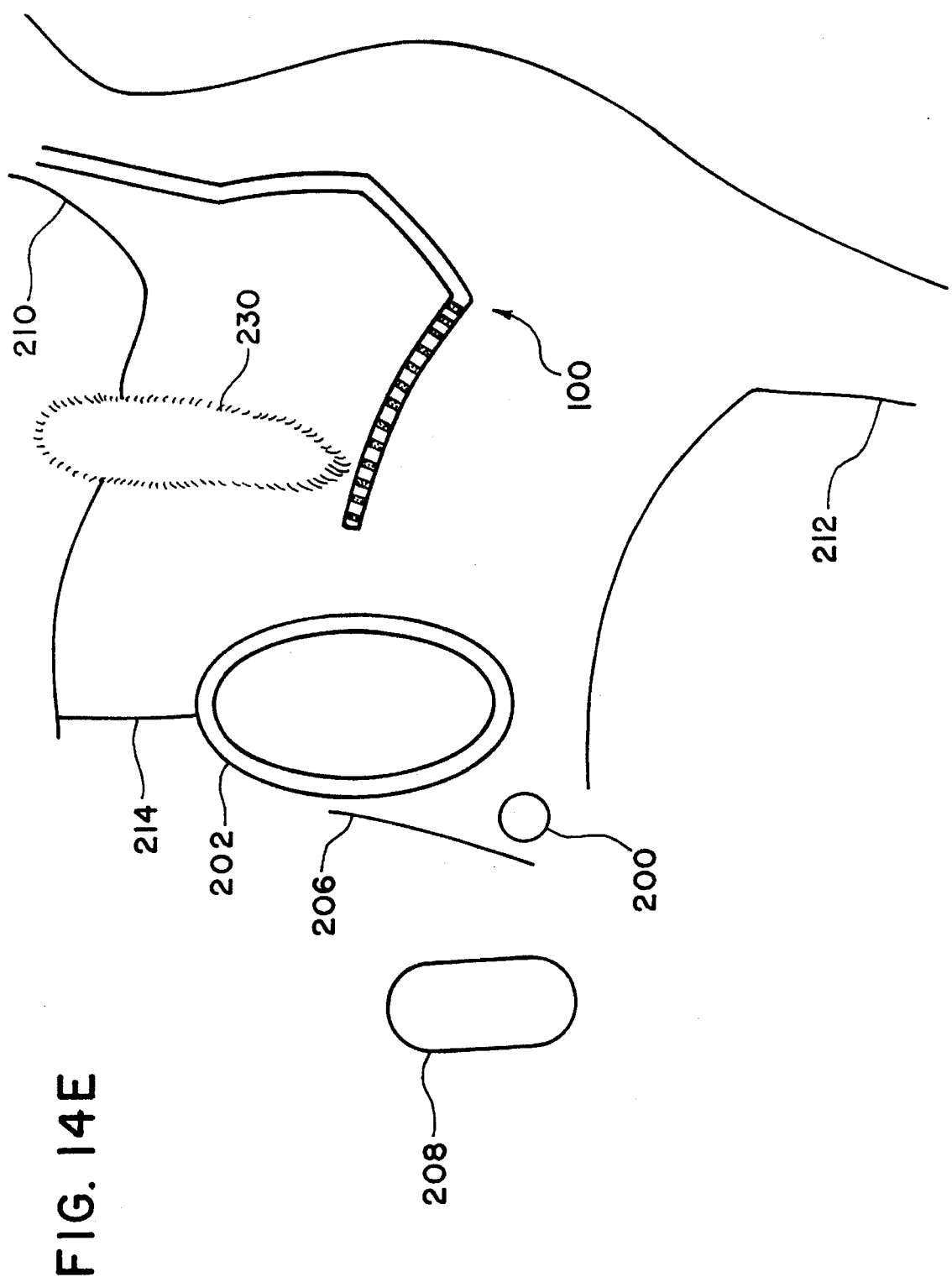
Figure 14F:
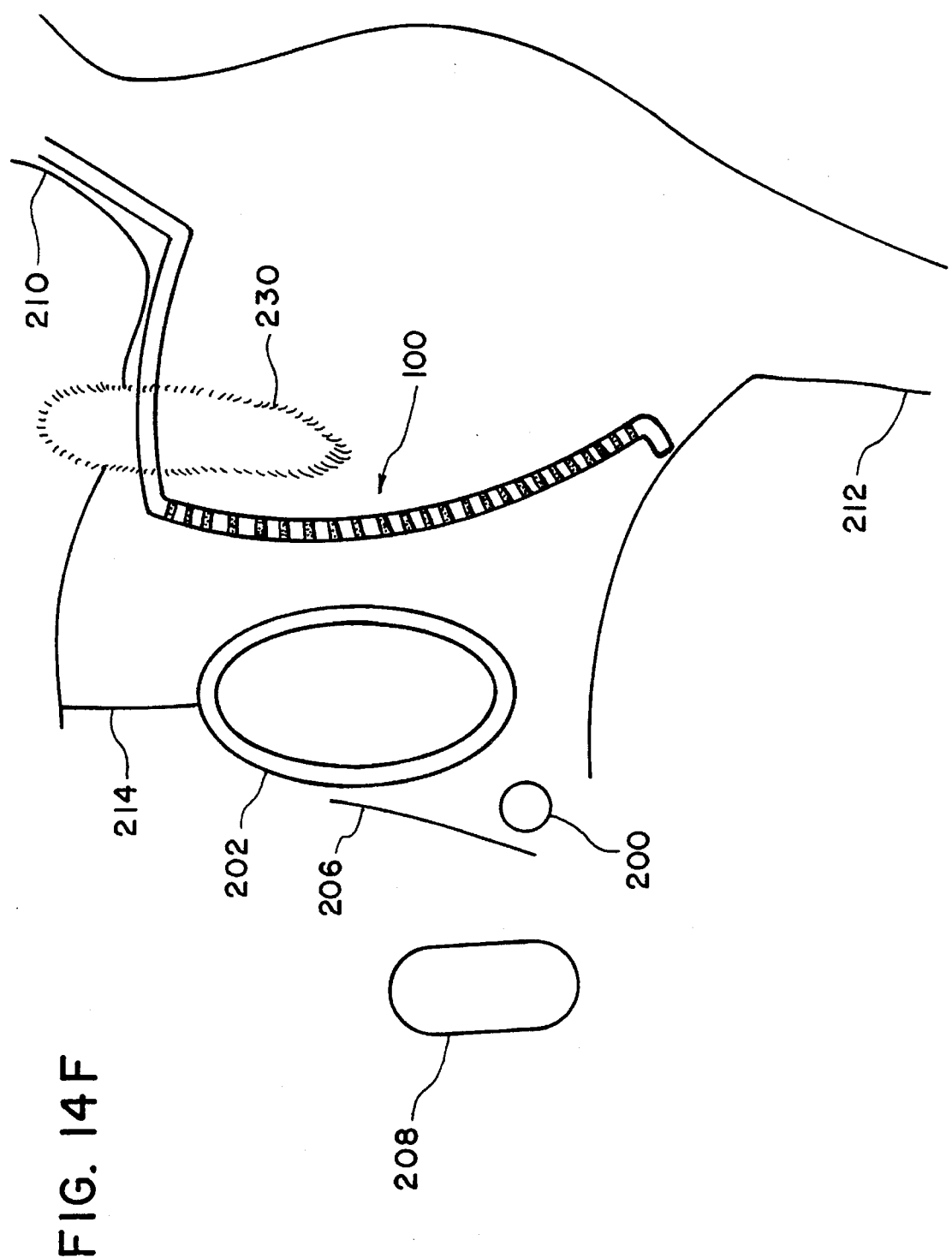
Figure 14G:
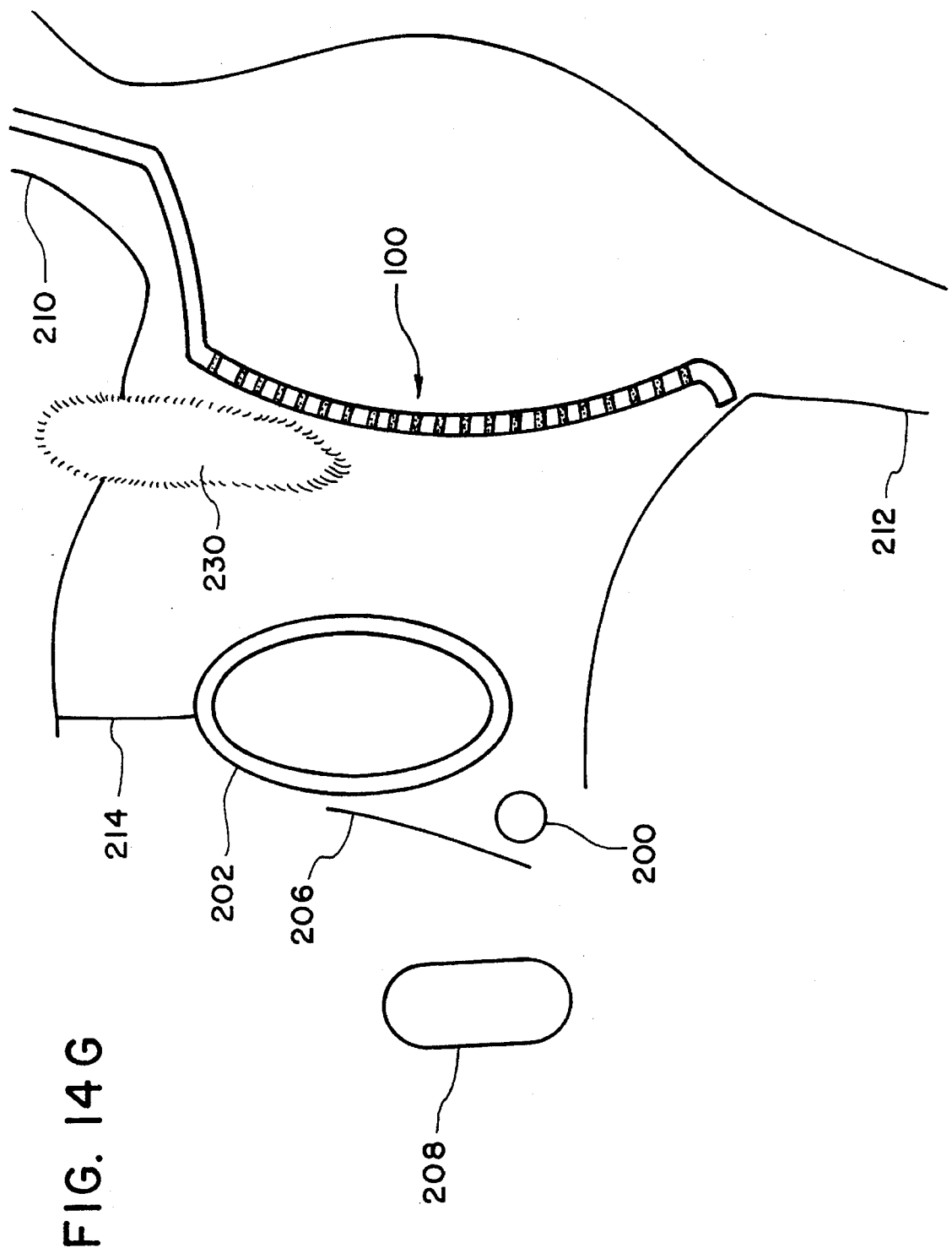
Figure 15:
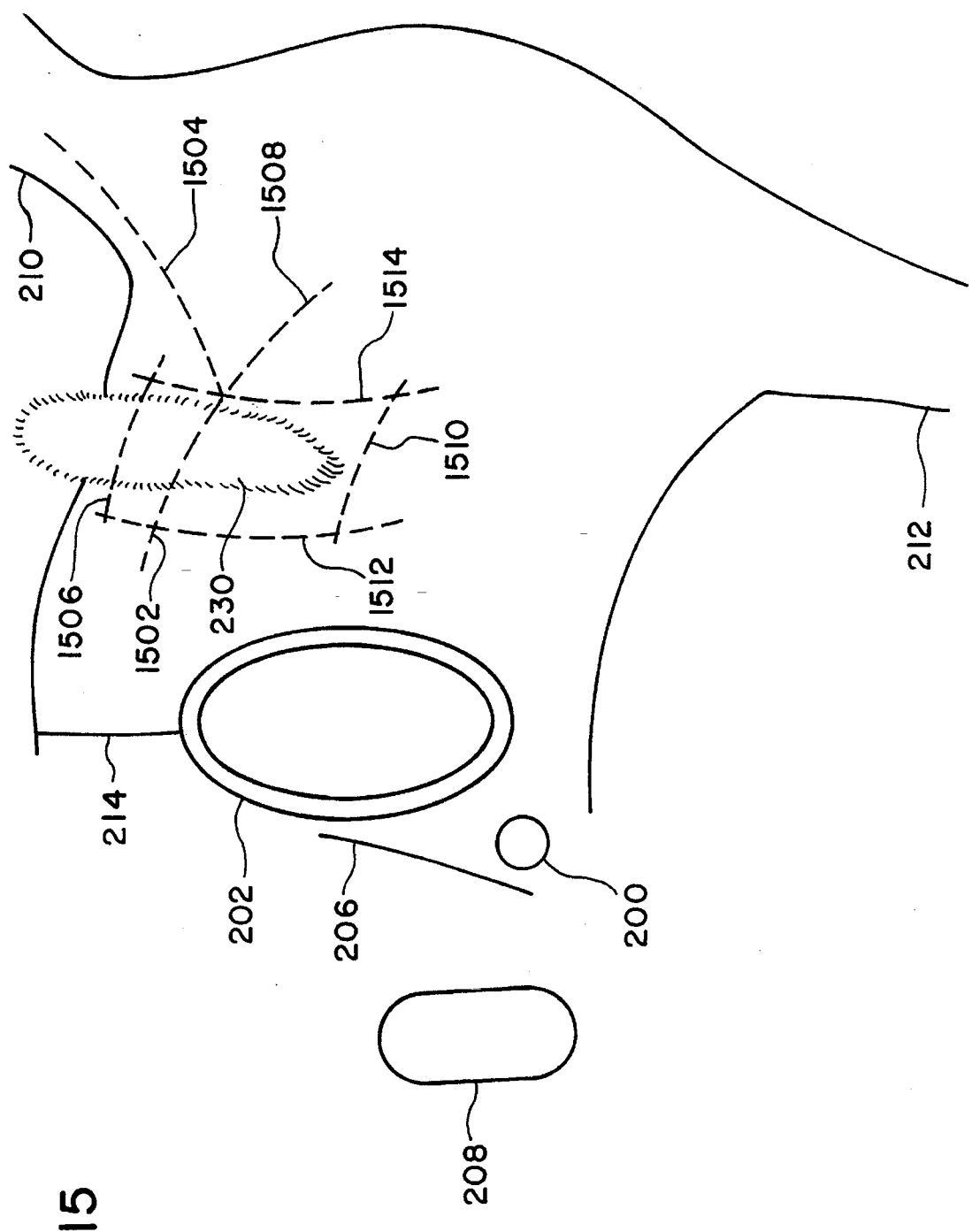
FIG. 15 illustrates a summary of ablation lesions that may be produced using multiple positions of the catheter as illustrated in FIGS. 14A–14G.

In that FIG. 15, the ablation line (1502) is created by positioning the catheter as shown in FIG. 14A, the ablation line (1504) is created by positioning the catheter as shown in FIG. 14B, the ablation line (1506) is created by positioning the catheter as shown in FIG. 14C, the ablation line (1508) is created by positioning the catheter as shown in FIG. 14D, the ablation line (15 10) is created by positioning the catheter as shown in FIG. 14E, the ablation line (1512) is created by positioning the catheter as shown in FIG. 14F, and the ablation line (1514) is created by positioning the catheter as shown in FIG. 14G.

FIGS. 16A through 16H show an exemplary catheter (100) in position in the left atrium (221). Entrance into the left atrium (221 ) is via the transseptal technique from the right atrium (203). Alternatively, the left atrium (221) may be accessed via the aorta, through the aortic valve, and via the mitral valve. FIGS. 16A through 16H illustrate positioning a catheter (100) using the transseptal technique. Note that in some instances, a catheter having the shape illustrated in FIG. 9A is used (e.g., in FIGS. 16E and 16F). The heart structures shown in those figures include the left atrial side of the interatrial septum (222), the posterior wall of the left atrium (224), the left atrial appendage (226), and the posterior aspect of the mitral valve ring (220). Pulmonary veins (228) also are shown.

Figure 16A:
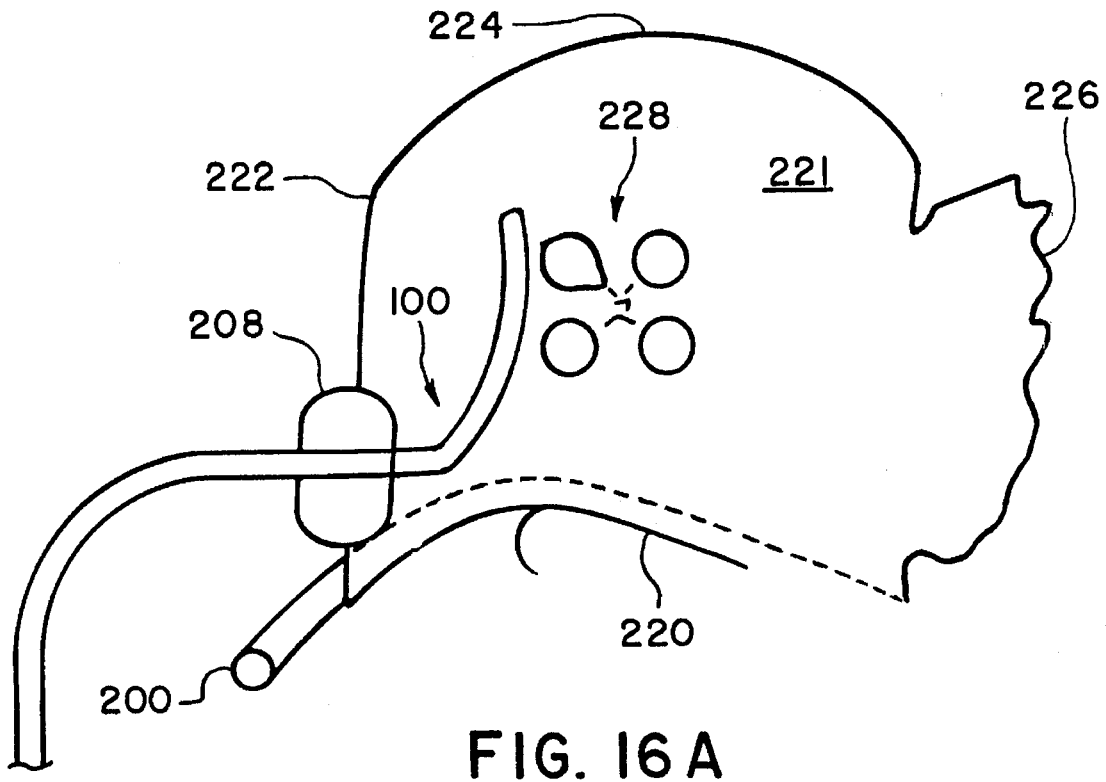
FIGS. 16A–16H show a catheter of the present invention in alternative positions in the left atrium.
Figure 16B:
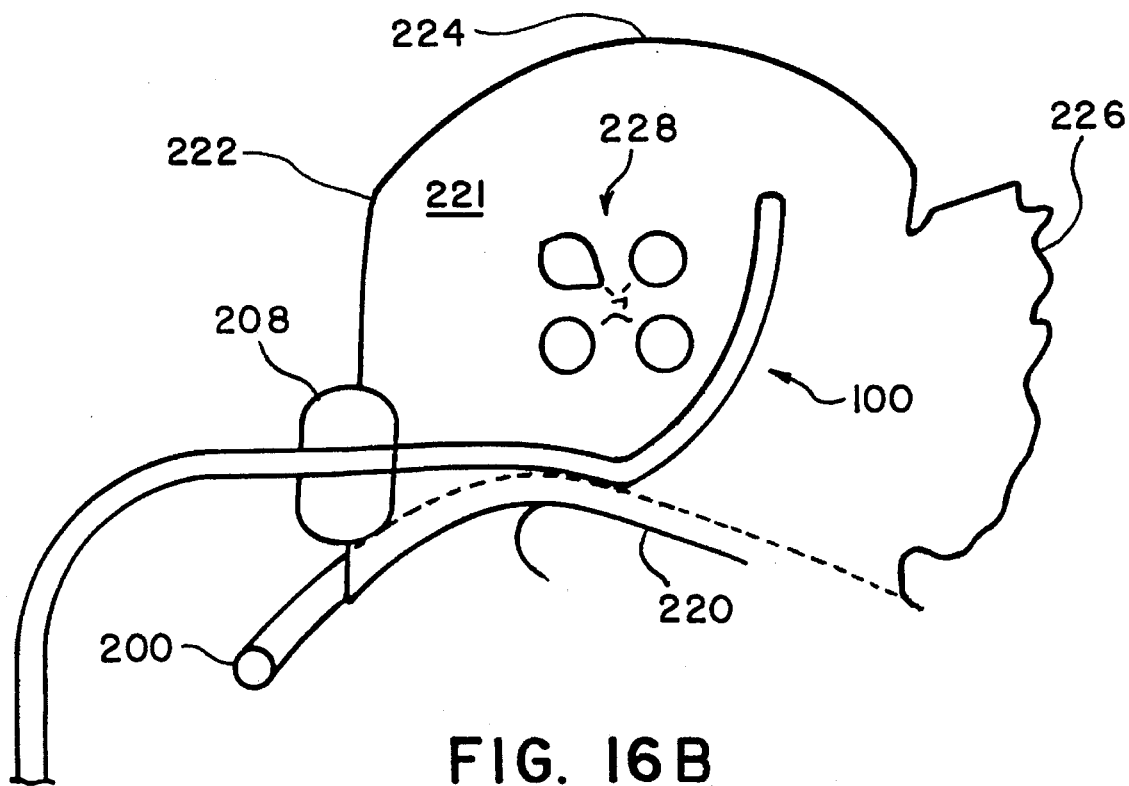
Figure 16C:
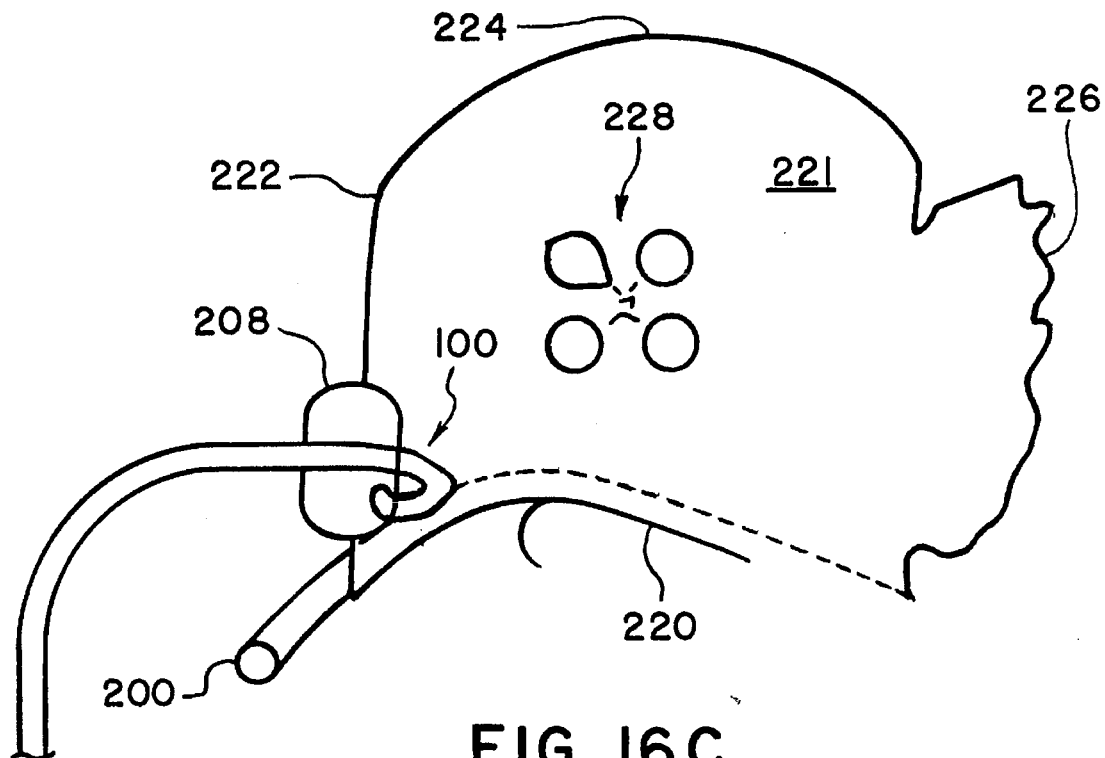
Figure 16D:
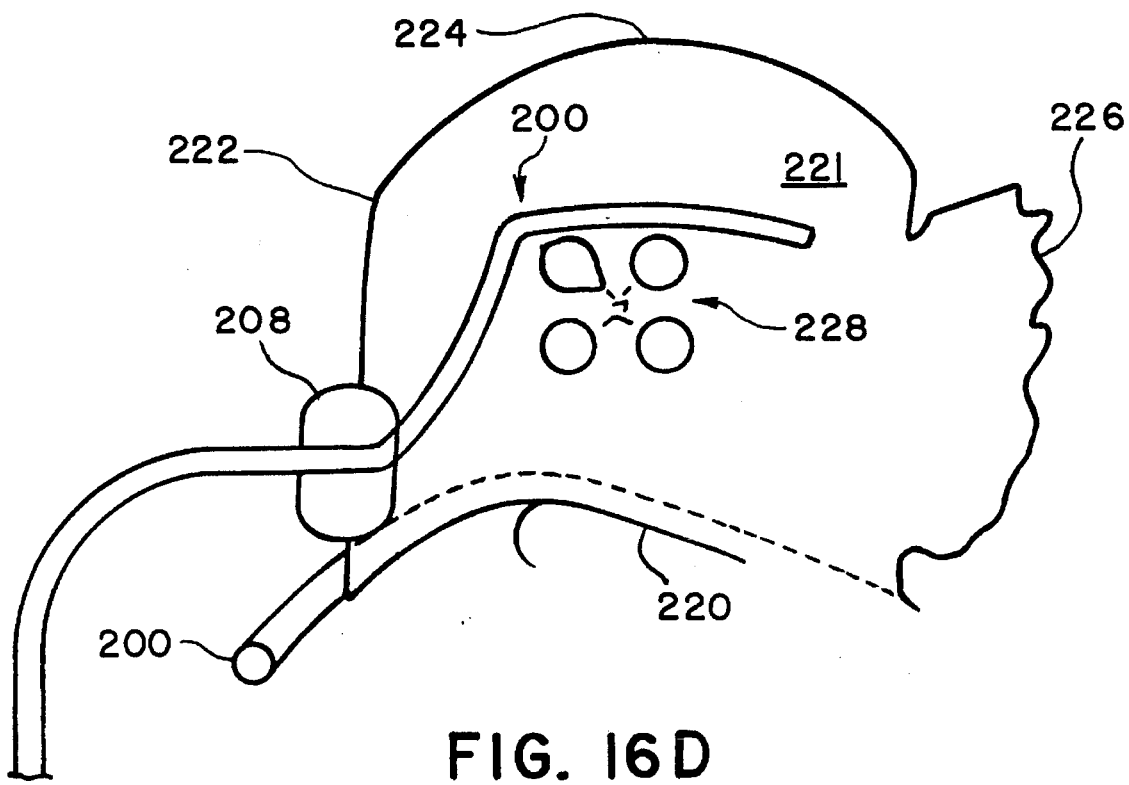
Figure 16E:
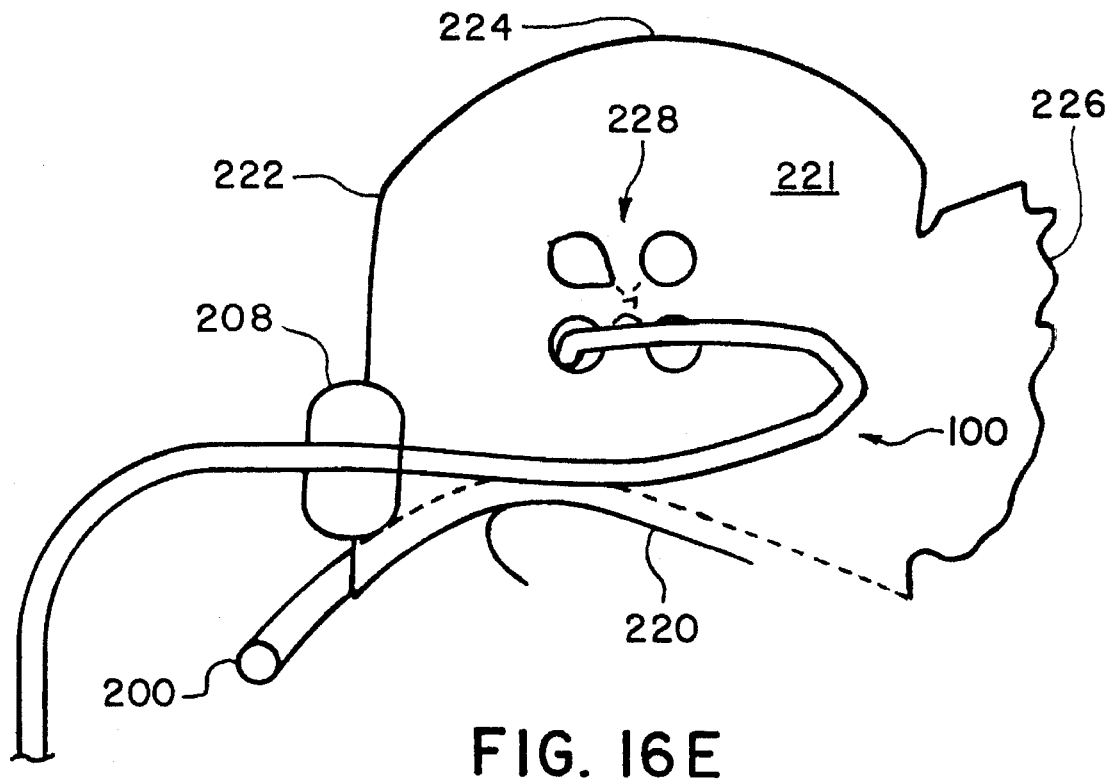
Figure 16F:
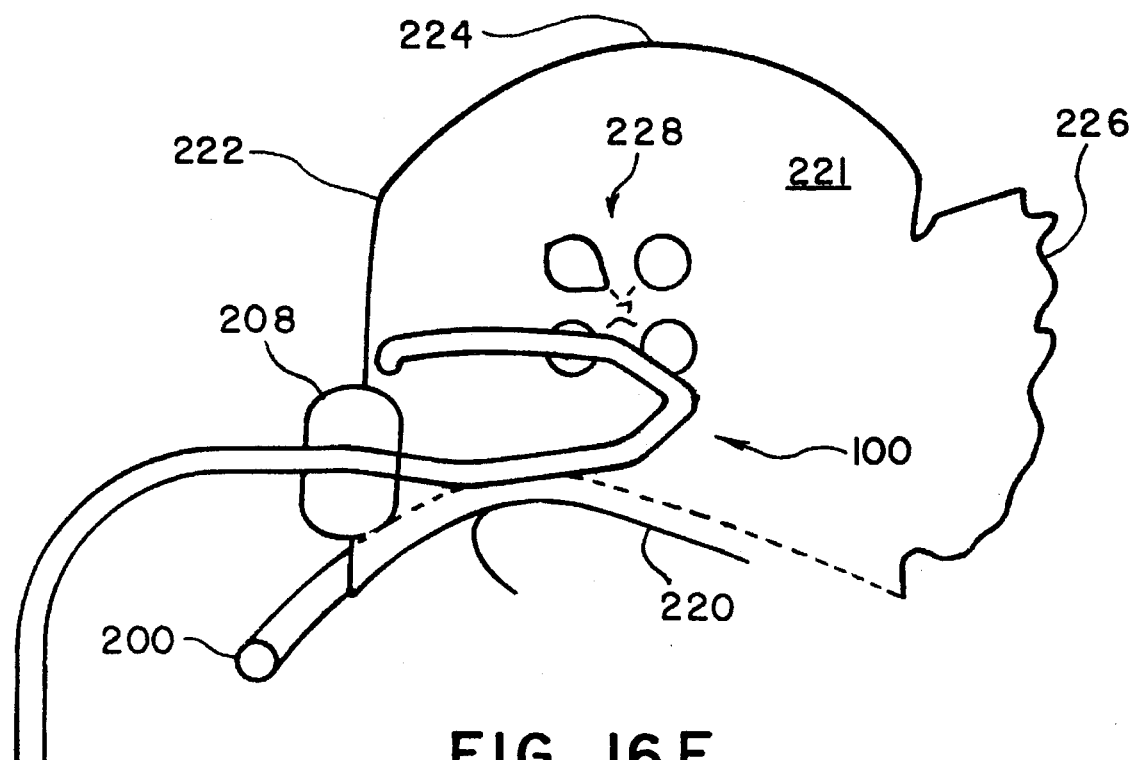
Figure 16G:
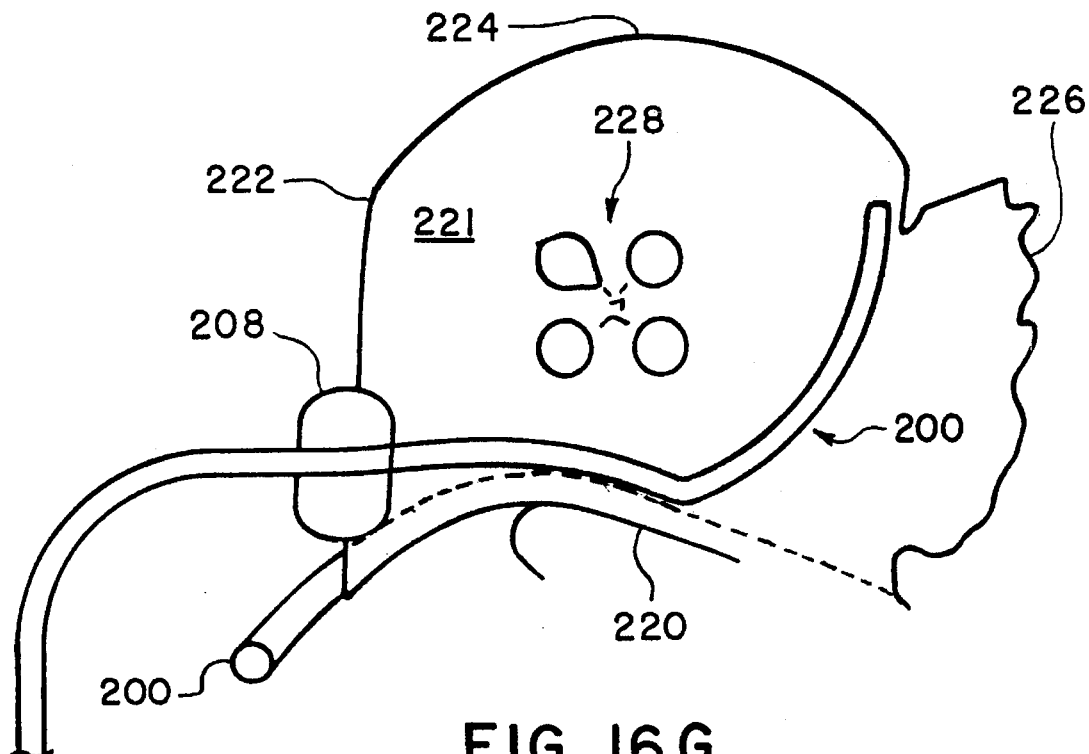
Figure 16H:
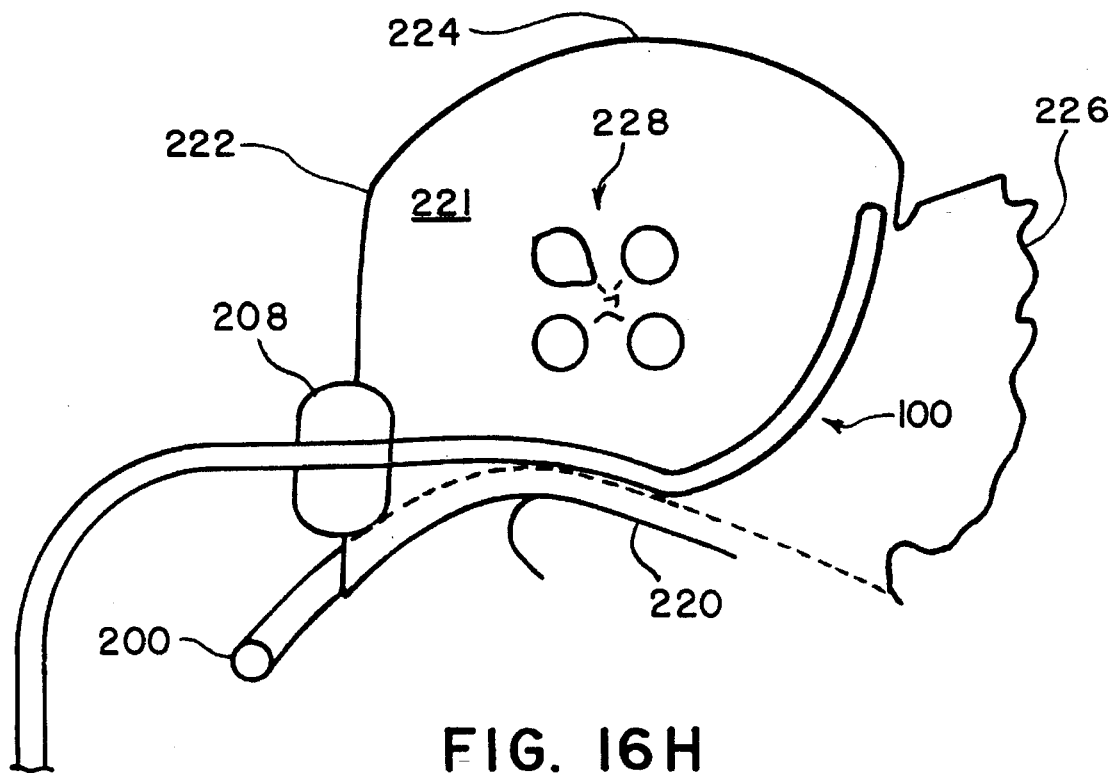

FIG. 17 illustrates the pattern of lesions resulting from ablating using the series of catheter positions shown in FIGS. 16A–16H. Specifically, the ablation line (1702) is created by positioning a catheter (100) as shown in FIG. 16A, the ablation line (1704) is created by positioning a catheter (100) as shown in FIG. 16B, the ablation line (1706) is created by positioning a catheter (100) as shown in FIG. 16C, the ablation line (1708) is created by positioning a catheter (100) as shown in FIG. 16D, the ablation line (1710) is created by positioning a catheter (100) as shown in FIG. 16E, the ablation line (17 12) is created by positioning a catheter (100) as shown in FIG. 16F, the ablation line (1714) is created by positioning a catheter (100) as shown in FIG. 16G, and the ablation line (1716) is created by positioning a catheter (100) as shown in FIG. 16H.

Figure 18:
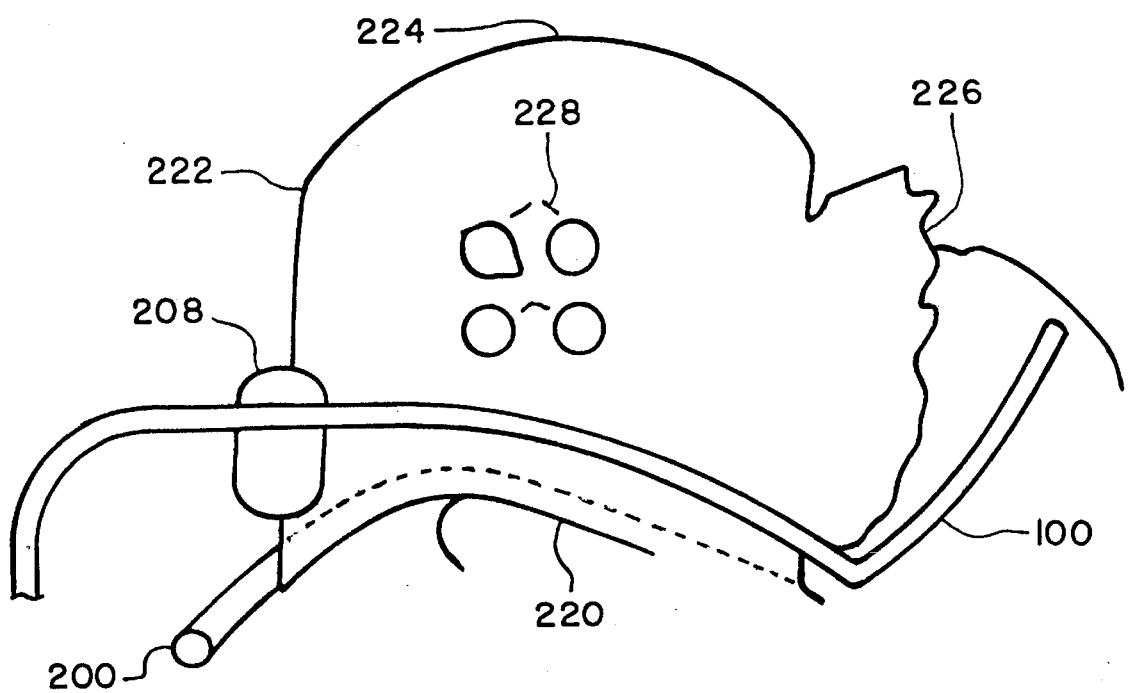
FIG. 18 shows a catheter of the present invention in position in the left atrium.
Figure 19:
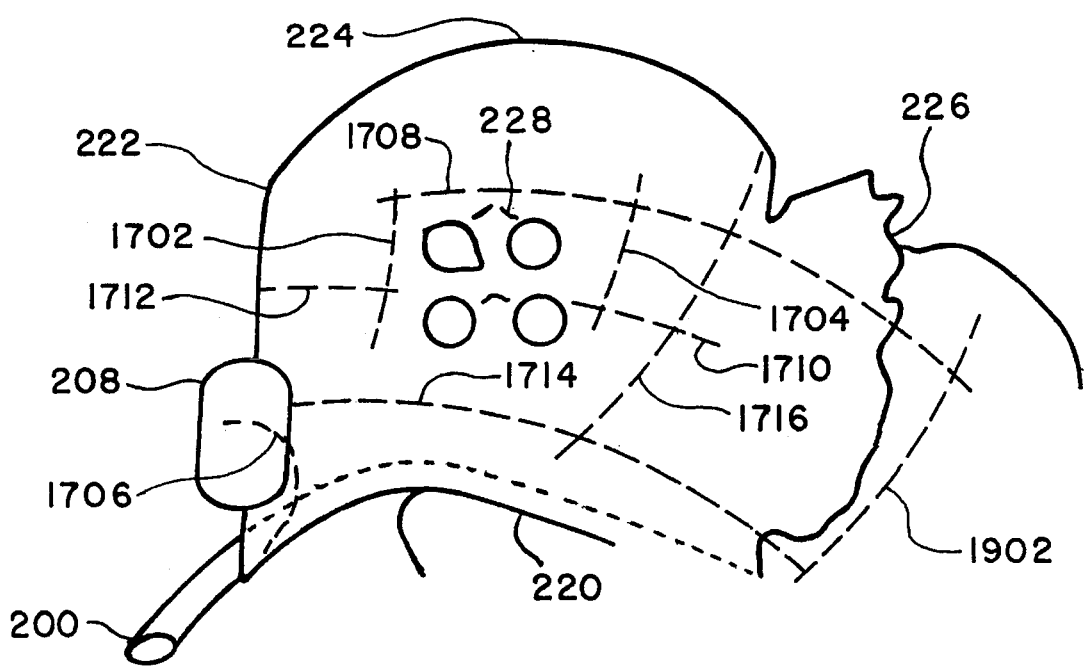
FIG. 19 shows a summary of lesions that may be produced using a combination of the catheter positions shown in FIGS. 16A–16H and in FIG. 18.

Alternatively, a catheter (100) may be positioned in the left atrium (221) as shown in FIG. 18. Thus, a lesion (1902 of FIG. 19) may be positioned on the anterior aspect of the atrial appendage so that it basically circumscribes the appendage. The lesion (1902) created by the catheter (100) thus positioned is shown in FIG. 19. As shown in that FIG. 19, the lesion (1902) preferably is combined with the lesions created as shown in FIG. 17 and in conjunction with the lesions created in the left atrium as shown in FIGS. 11 or 13.

FIGS. 20A through 20G show a catheter (100) in position in the left atrium (221) through the inferior vena cava (212) to ablate atrial circuitry. Those FIGURES show lesions made for the anterior aspect of the right atrial appendage (230) from the groin. The ablation pattern made by application of each of these catheters in the illustrated positions is shown in FIG. 21.

Figure 20B:
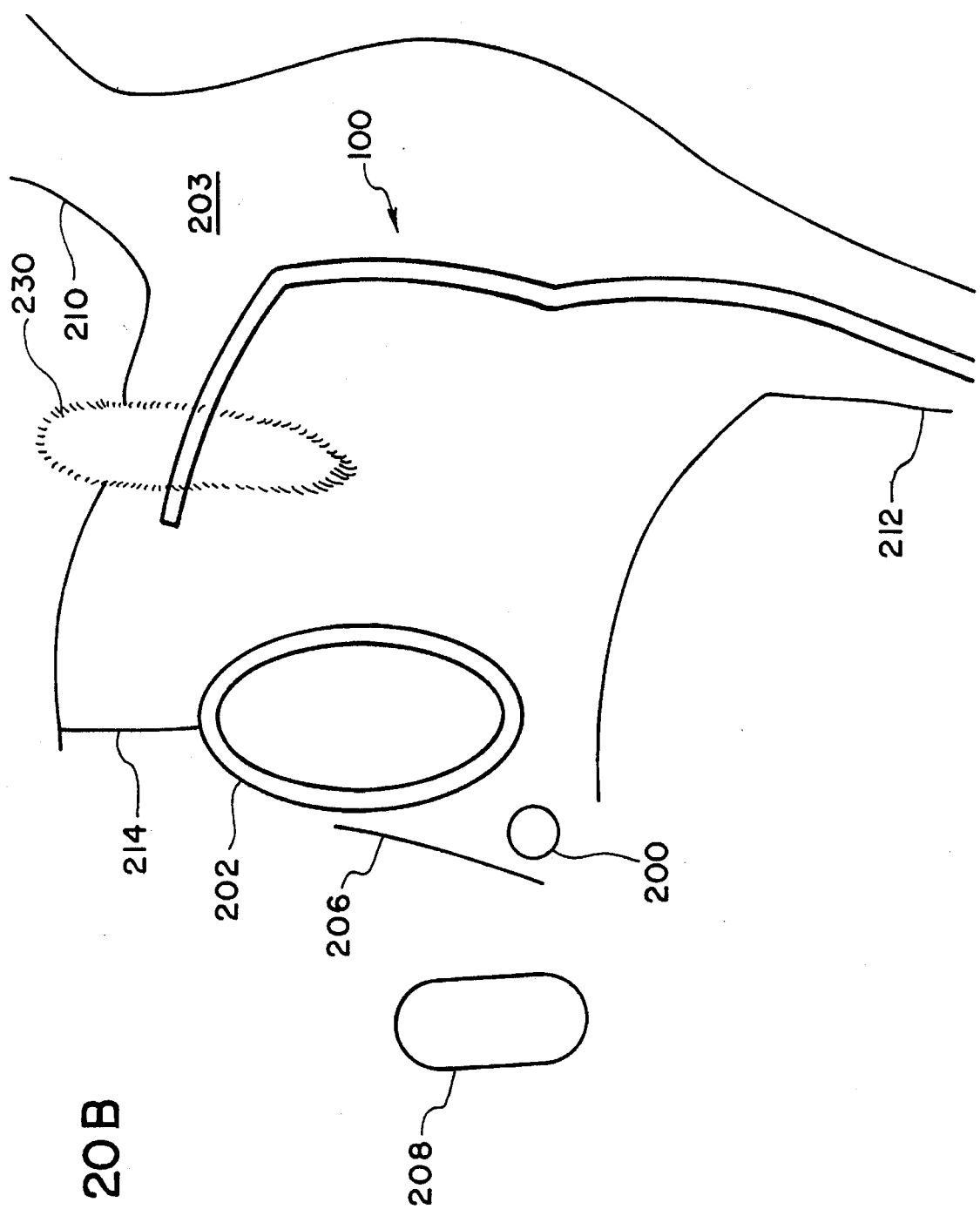
Figure 20C:
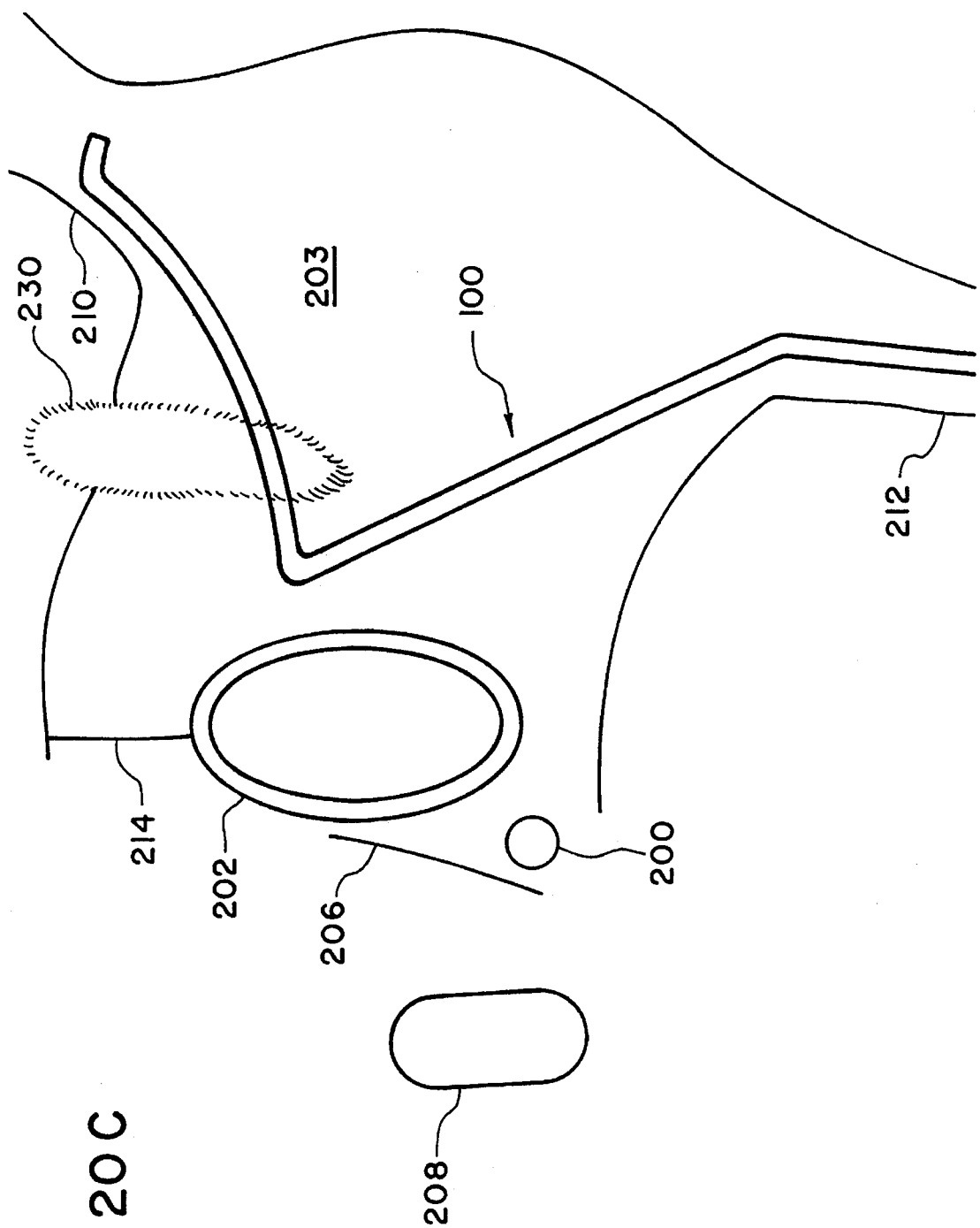
Figure 20D:
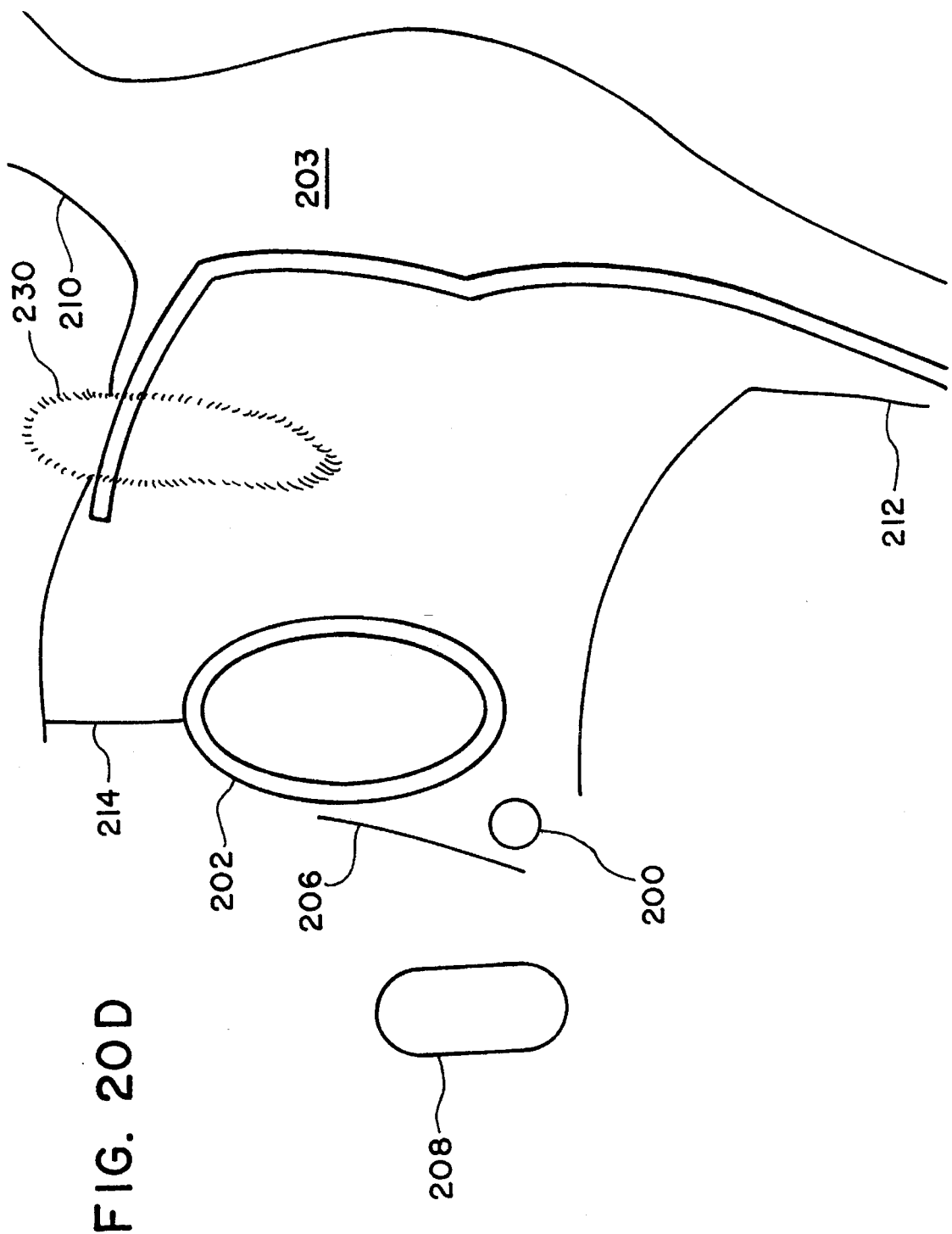
Figure 20E:
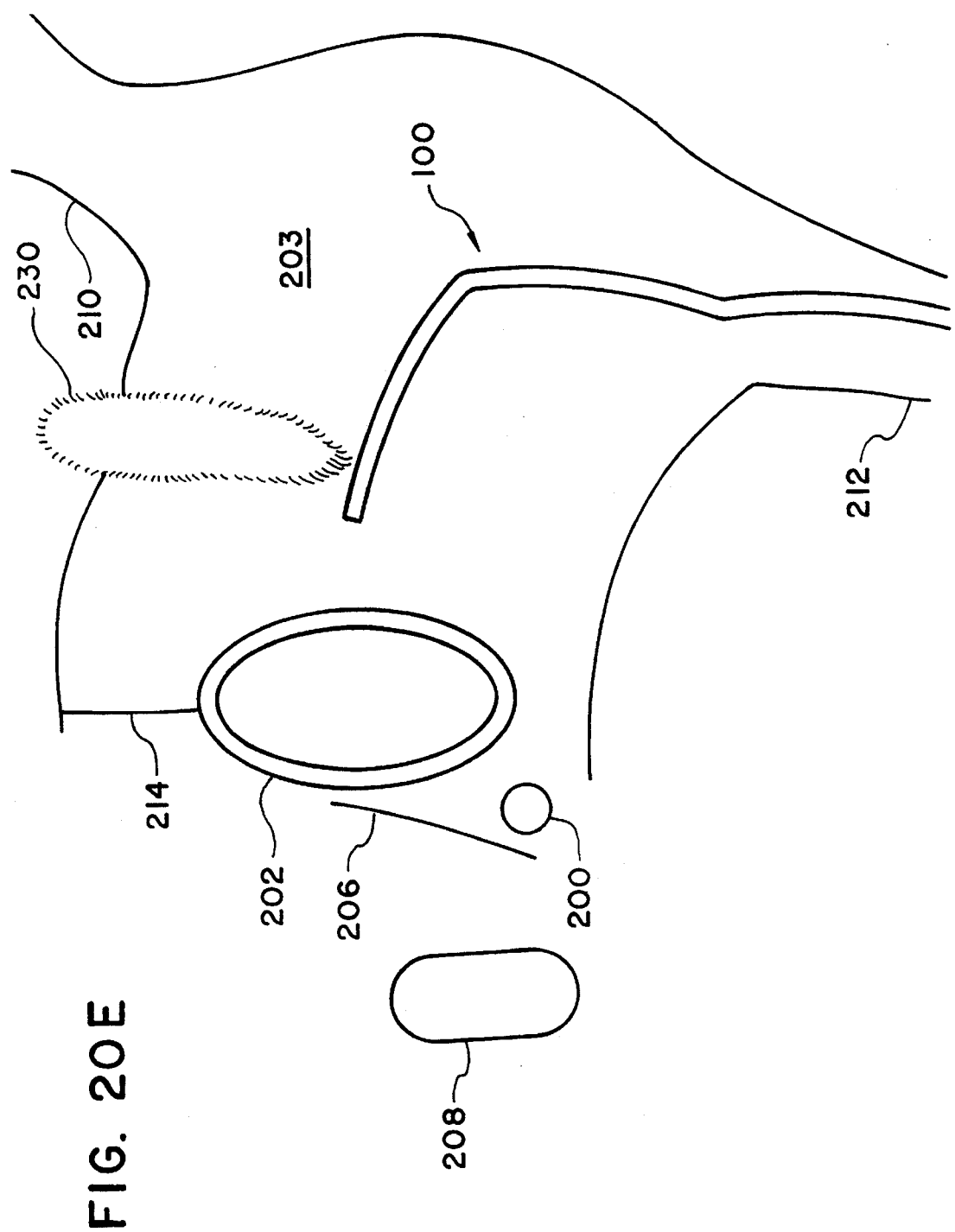
Figure 20F:
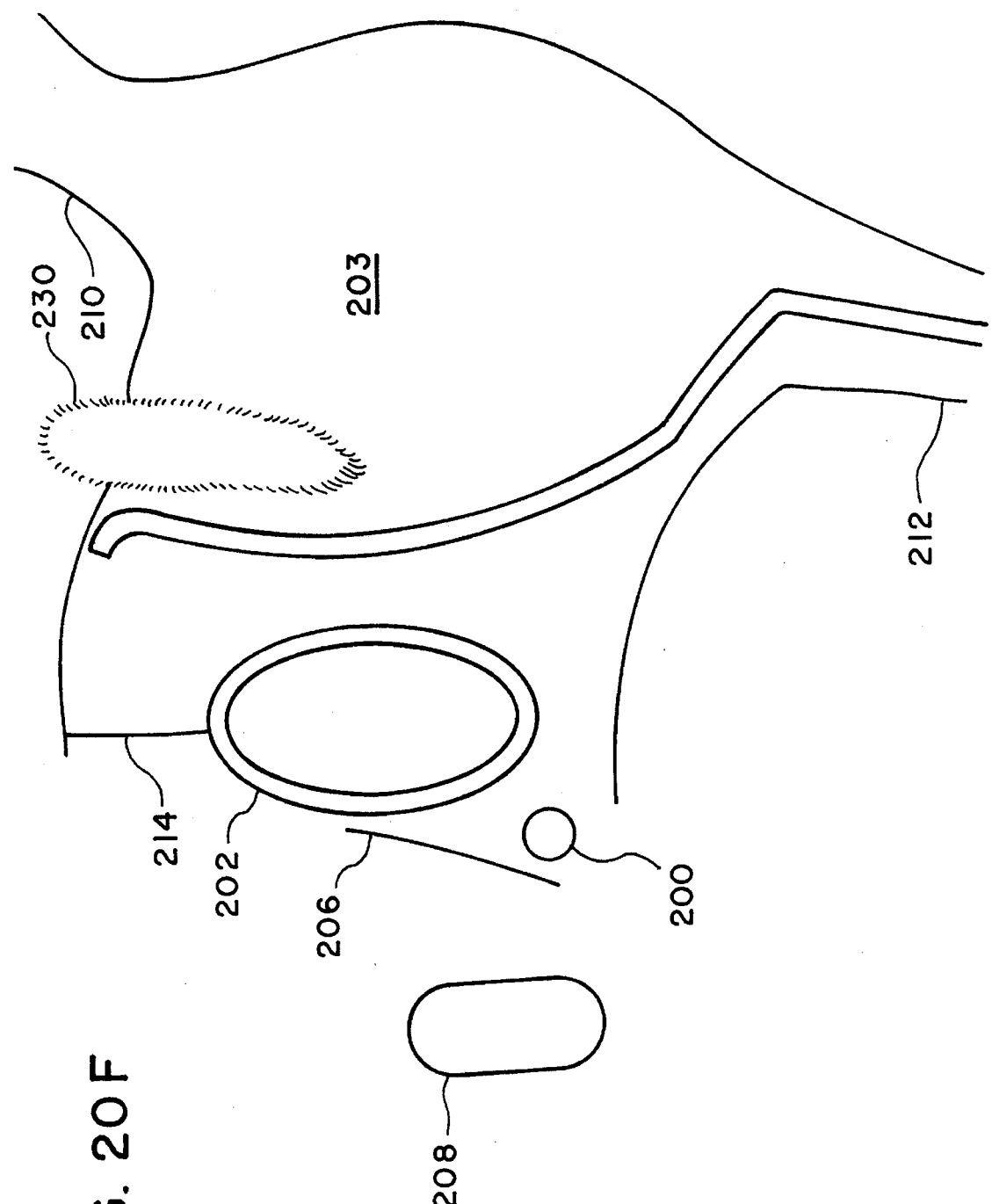
Figure 20G:
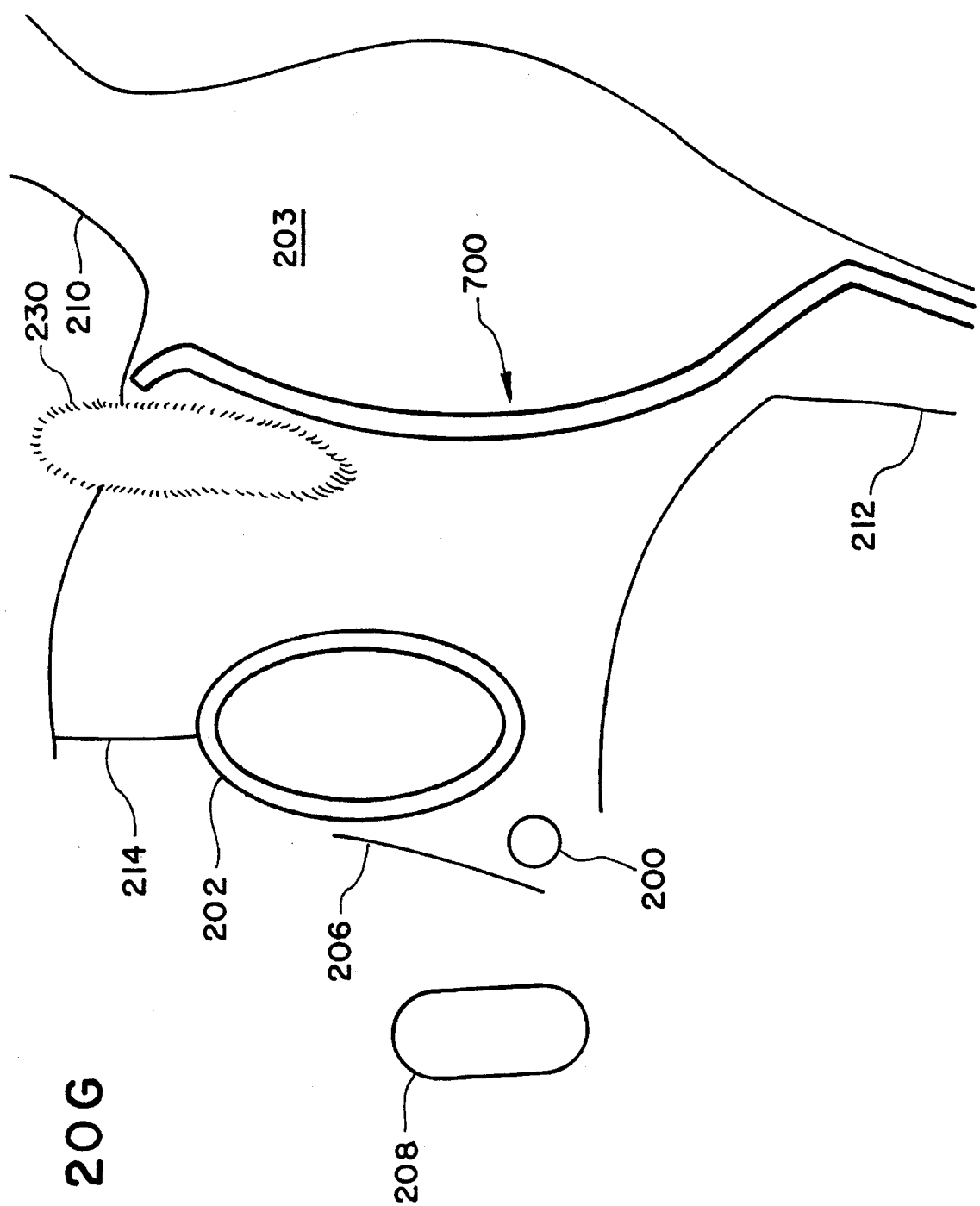
Figure 21:
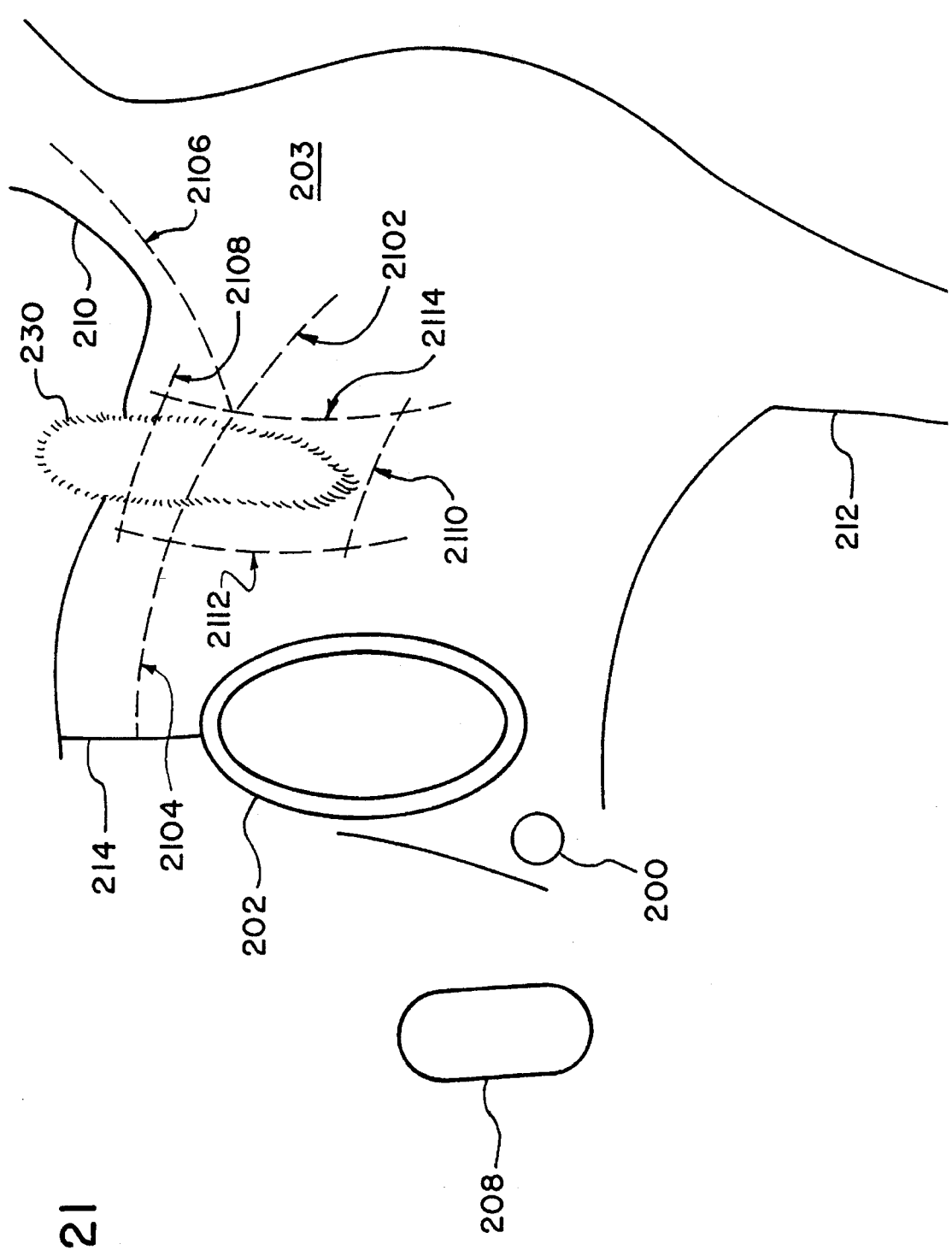
FIG. 21 shows a summary of lesions that may be produced using a combination of the catheter positions shown in FIGS. 20A–20G.

In that FIG. 21, the ablation line (2102) is created by positioning the catheter as shown in FIG. 20B, the ablation line (2104) is created by positioning the catheter as shown in FIG. 20A, the ablation line (2106) is created by positioning the catheter as shown in FIG. 20C, the ablation line (2108) is created by positioning the catheter as shown in FIG. 20D, the ablation line (2110) is created by positioning the catheter as shown in FIG. 20E, the ablation line (2112) is created by positioning the catheter as shown in FIG. 20F, and the ablation line (2114) is created by positioning the catheter as shown in FIG. 14G.

The lesion pattern shown in FIG. 21 is preferred when using a "maze" type procedure to provide lesions around the right atrial appendage (230). This is regardless of whether one is doing the procedure from the inferior vena cava (212) or the superior vena cava (210). A complete "maze" type procedure would include either one of the right atrium access sites, i.e., the inferior (212) or superior (210) vena cava, plus either one of the left atrial access sites, i.e., trans-septal or retrograde aortic, and the lesions produced by each. Thus, a complete "maze" type procedure would include all lesions shown in FIGS. 13, 15, 19, and 21.

Other variations, modifications, and materials substitutions will be apparent to those skilled in the relevant art. In addition, the specific shape of the catheter (100) may depend on the specific condition intended to be treated, or the particular area of the heart being mapped.

What is claimed is:

1. A cardiac catheter apparatus for treating atrial fibrillation by selectively mapping and ablating target endocardial portions of predefined cardiac circuitry in atrial cardiac chambers which comprises a plurality of individual preshaped catheters, each catheter comprising:

A. a preshaped, flexible, elongate tubular member manufactured of biocompatible shape memory material having a distal end and a proximal end and at least one lumen extending from said proximal end to said distal end;

B. a guide-wire slidably engaged within said lumen and extending an amount beyond said distal end of said tubular member;

C. a preshaped first curved portion at said distal end of said tubular member for positioning at a target portion of a cardiac chamber upon removal of said guide-wire;

D. a shaft at said proximal end of said tubular member;

E. a means for connecting said first curved portion and said shaft comprising at least one preshaped portion selected from the group consisting of one or more intermediate preshaped curved portions, one or more intermediate preshaped straight portions and combinations thereof;

F. an array of spaced-apart electrodes positioned around an outer surface of at least one part of at least one preshaped portion of said tubular member; and G. insulated conductor means electrically connecting the individual electrodes to means outside of the catheter for selectively mapping and ablating electrically target portions of cardiac tissue adjacent said electrodes in said cardiac chamber; said plurality of catheters including one catheter having a partially circular shaped distal portion, one catheter having a V-shaped distal portion, one catheter have a distal portion shaped for positioning horizontally of a cardiac chamber and one catheter having a distal portion shaped for positioning vertically of a cardiac chamber whereby lesions formed by the ablations produced by said plurality of catheters create an electrical maze pattern of the same type resulting from a surgical procedure for treating atrial fibrillation.

2. The cardiac catheter apparatus of claim 1 wherein said catheter having a partially circular shaped distal portion further includes second and third curved intermediate preshaped portions continuous with said first curved portion for securing said first curved portion around the ostium of the coronary sinus in a cardiac chamber upon the removal of said guide-wire and for increasing contact of said catheter with a target portion of tissue in said cardiac chamber.

3. The cardiac catheter apparatus of claim 1 wherein said catheter having a distal portion shaped for positioning vertically in a cardiac chamber further includes second and third intermediate curved portions continuous with said first curved portion and a notch positioned below said third curved portion, said notch being designed to fit a side of a mitral annulus located in a cardiac chamber thereby securing the catheter in position at said target portion.

4. The cardiac catheter apparatus of claim 1 wherein said plurality of catheters includes less than all of said preshaped catheters, said apparatus being effective to overcome atrial fibrillation by ablations which do not create said electrical maze pattern.

5. The cardiac catheter apparatus of claim 1, wherein the shape memory material comprises nitinol.

6. A cardiac catheter apparatus for treating atrial fibrillation by selectively mapping and ablating target endocardial portions of predefined cardiac circuitry in atrial cardiac chambers which comprises a plurality of individual catheter assemblies, each catheter assembly comprising:

A. a sheath assembly, including an elongate tubular sheath having a distal end and a proximal end and a lumen therethrough and a guide-wire slidably engaged within said lumen and extending an amount beyond said distal end of said sheath; and B. a preshaped catheter manufactured of biocompatible shape memory material for slidable engagement within said lumen after said sheath is positioned proximal to a target portion of a cardiac chamber and after removal of said guide-wire, said catheter comprising:

1. a preshaped, flexible, elongate tubular member made of shape memory material having a distal end and a proximal end;

2. a preshaped first curved portion at said distal end for positioning at a target portion of a cardiac chamber;

3. a shaft at said proximal end of said catheter;

4. a means for connecting said first curved portion and said shaft comprising at least one preshaped portion selected from the group consisting of one or more intermediate preshaped curved portions, one or more intermediate preshaped straight portions and combinations thereof;

5. an array of spaced-apart electrodes positioned around an outer surface of at least one part of at least one preshaped portion of said catheter; and 6. insulated conductor means electrically connecting the individual electrodes to a means outside of said catheter for selectively recording and ablating electrically target portions of cardiac tissue adjacent said electrodes in said cardiac chamber; said plurality of catheter assemblies including one assembly having a catheter having a partially circular shaped distal portion, one assembly having a catheter having a V-shaped distal portion, one assembly having a catheter having a distal portion shaped for positioning horizontally in a cardiac chamber and one assembly having a distal portion shaped for positioning vertically in a cardiac chamber whereby lesions formed by the ablations produced by said catheters create an electrical maze pattern of the same type resulting from a surgical procedure for treating atrial fibrillation.

7. The cardiac catheter apparatus of claim 6 wherein said catheter having a partially circular shaped distal portion further includes second and third curved intermediate preshaped portions continuous with said first curved portion for securing said first curved portion around the ostium of a coronary sinus in the right atrium and for increasing contact of said catheter with a target tissue portion in said atrium.

8. The cardiac catheter apparatus of claim 6 wherein said catheter having a distal portion shaped for positioning vertically in a cardiac chamber further includes second and third intermediate curved portions continuous with said first curved portion and a notch positioned below said third curved portion, said notch being designed to fit a side of the right atrium thereby securing the catheter in position at said target portion.

9. The cardiac catheter apparatus of claim 6 wherein each catheter assembly further includes a substantially solid dilator between said sheath and said lumen.

10. The cardiac catheter apparatus of claim 6 wherein said plurality of catheter assemblies includes less than all of said assemblies, said apparatus being effective to overcome atrial fibrillation by ablations which do not create said electrical maze pattern.

11. The cardiac catheter of claim 6, wherein the shape memory material comprises nitinol.

12. A method for treating atrial fibrillation by selectively disrupting predetermined target endocardial portions of predefined cardiac circuitry in atrial cardiac chambers which employs a plurality of cardiac catheters, each catheter comprising (I) a preshaped, flexible, elongate, tubular member manufactured of biocompatible shape memory material having a distal end and a proximal end and a lumen extending from said proximal end to said distal end; (II) a guide-wire slidably engaged within said lumen and extending an amount beyond the distal end of said tubular member; (III) a preshaped first curved portion at said distal end of said tubular member for positioning proximal to a target portion of an atrium upon removal of said guide-wire; (IV) a shaft at the proximal end of said tubular member; (V) a means for connecting said first curved portion and said shaft comprising at least one preshaped portion selected from the group consisting of one or more intermediate preshaped curved portions, one or more intermediate straight portions and combinations thereof; (VI) an array of spaced-apart electrodes positioned around an outer surface of at least one part of at least one preshaped portion of said tubular member; and (VII) insulated conductor means for electrically connecting the individual electrodes to a device outside of the catheter for selectively mapping and ablating electrically target portions of cardiac tissue adjacent said electrodes in said atrial cardiac chamber; which method comprises the steps of:

A. introducing through a blood vessel a cardiac catheter containing a tubular member selected from the group consisting of a tubular member having a partially circular shaped distal portion, a tubular member having a V-shaped distal portion, a tubular member having a distal portion shaped for positioning horizontally in a cardiac chamber and a tubular member having a distal portion shaped for positioning vertically in a cardiac chamber into a cardiac chamber proximal to a target portion of said chamber;

B. removing said guide-wire from within said tubular member to shape said distal portion of said tubular member to its preshaped form;

C. recording one or more satisfactory depolarization potentials from the tissue at said target portion;

D. remotely activating at least one of the electrodes on said catheter to a preselected current level for a preselected time interval to selectively ablate said target portion of said cardiac circuitry to produce a lesion;

E. removing said catheter from said cardiac chambers; and

F. repeating steps A–D above sequentially with each individual catheter set forth in the group in A above other than the catheter used in step A above and repositioning said catheters for positioning horizontally and vertically in a cardiac chamber until steps A–E reproduce the pattern of lesions shown in FIGS. 13, 15, 19 and 21 with the exception that when said catheters are repositioned in a cardiac chamber, step A consists of reintroducing said guide wire and step D is omitted until said catheter is positioned proximal to its final target portion; whereby the resultant multiple lesions create an electrical maze of the same type resulting from a surgical procedure for treating atrial fibrillation.

13. The method of claim 12 wherein the step of introducing at least one of said catheters is through a great vein until the tip of said guide-wire rests across a tricuspid valve.

14. The method of claim 12 wherein the step of introducing at least one of said catheters is through a blood vessel passageway selected from the group consisting of the superior vena cava and the inferior vena cava.

15. The method of claim 12 wherein the electrode is activated to said preselected current level using between about 15 volts and about 40 volts.

16. The method of claim 12 wherein the electrode is activated for a preselected time interval of between about 25 seconds and 35 seconds.

17. The method of claim 12 wherein step F consists of repeating steps A–D with less than all of the individual catheters set forth in Group A, said method being effective to overcome atrial fibrillation by ablations which do not create said electrical maze pattern.

18. The method for treating atrial fibrillation by selectively disrupting predetermined target endocardial portions of predefined cardiac circuitry in atrial cardiac chambers which employs a plurality of individual catheter assemblies, each catheter assembly comprising (A) a sheath assembly, including an elongate tubular sheath having a distal end and a proximal end and a lumen therethrough and a guide-wire slidably engaged within said lumen and (B) a preshaped catheter manufactured of biocompatible shape memory material for slidable engagement within said lumen after said sheath is positioned proximal to a target portion of a cardiac chamber and after removal of said guide-wire, said catheter comprising: (1) a preshaped, flexible, elongate tubular member having a distal end and a proximal end; (2) a preshaped first curved portion at said distal end for positioning proximal to a target portion of a cardiac chamber; (3) a shaft at said proximal end of said catheter; (4) a means for connecting said first curved portion and said shaft comprising at least one preshaped portion selected from the group consisting of one or more intermediate preshaped curved portions, one or more intermediate preshaped straight portions and combinations thereof; (5) an array of spaced-apart electrodes positioned around an outer surface of at least one part of at least one preshaped portion of said catheter; and (6) insulated conductor means electrically connecting the individual electrodes to means outside of said catheter for selectively mapping and ablating electrically a target portion of cardiac tissue adjacent said electrodes in said cardiac chamber; which method comprises the steps of:

A. introducing a catheter assembly selected from the group consisting of catheter assemblies which include a catheter with a preshaped distal portion selected from the group consisting of a catheter having a partially circular shaped distal portionr, a catheter having a V-shaped distal portion, a catheter having a distal portion shaped for positioning horizontally in a cardiac chamber and a catheter having a distal portion shaped for positioning vertically in a cardiac chamber through a blood vessel into a cardiac chamber proximal to a target portion of said chamber, B. benching said guide-wire;

C. advancing said sheath over said guide-wire;

D. withdrawing said guide-wire from said chamber and said blood vessel;

E. introducing said catheter through said sheath into said cardiac chamber;

F. benching said catheter at said target position;

G. withdrawing said sheath such that said distal portion of said catheter is positioned at said target position;

H. recording one or more satisfactory depolarization potentials from the cardiac tissue at said target portion;

I. remotely activating at least one of the electrodes on said catheter to a preselected current level for a preselected time interval to selectively ablate said target portion of said cardiac circuitry to produce a lesion;

J. removing said catheter from said cardiac chamber; and

K. repeating steps A–J above sequentially with each catheter assembly set forth in A above other than the catheter used in step A and repositioning catheters for positioning horizontally and vertically in a cardiac chamber until steps A–J reproduce the positions shown in FIGS. 13, 15, 19 and 21 with the exception that when said catheters are repositioned step A consists of reintroducing said sheath and said guide wire through said blood vessel into a cardiac chamber at a target portion of said chamber; whereby the resultant multiple lesions create an electrical maze of the same type resulting from a surgical procedure for treating atrial fibrillation.

19. The method of claim 18 wherein the step of introducing said catheter assembly comprises introducing the catheter sheath/guide-wire assembly through one of the blood vessel passageways including the superior vena cava and the inferior vena cava.

20. The method of claim 18 wherein the electrode is activated to said preselected current level using between about 15 volts and 40 volts for ablation of said target tissue.

21. The method of claim 20 wherein the electrode is activated for said preselected time interval of between about 25 seconds and about 35 seconds.

22. The method of claim 18 wherein step K consists of repeating steps A–J with less than all of the individual catheter assemblies set forth in Group A, said method being effective to overcome atrial fibrillation by ablations which do not create said electrical maze pattern.

23. A cardiac catheter for selectively mapping and ablating target endocardial portions of predefined cardiac circuitry in atrial cardiac chambers which comprises:

A. a preshaped, flexible, elongate tubular member manufactured of biocompatible shape memory material having a distal end and a proximal end and at least one lumen extending from said proximal end to said distal end;

B. a guide-wire slidably engaged within said lumen and extending an amount beyond said distal end of said tubular member;

C. a preshaped portion at said distal end of said tubular member for positioning at a target portion of a cardiac chamber upon removal of said guide-wire;

D. a shaft at said proximal end of said tubular member;

E. an array of spaced-apart electrodes positioned around an outer surface of at least one part of said preshaped distal portion of said tubular member; and F. insulated conductor means electrically connecting the individual electrodes to means outside of the catheter for selectively mapping and ablating electrically target portions of cardiac tissue adjacent said electrodes in said cardiac chamber.

24. A cardiac catheter assembly for selectively mapping and ablating target endocardial portions of predefined cardiac circuitry in atrial cardiac chambers which comprises:

A. a sheath assembly, including an elongate tubular sheath having a distal end and a proximal end and a lumen therethrough and a guide-wire slidably engaged within said lumen and extending an amount beyond said distal end of said sheath; and B. a preshaped catheter manufactured of biocmpatible shape memory material for slidable engagement within said lumen after said sheath is positioned proximal to a target portion of a cardiac chamber and after removal of said guide-wire, said catheter comprising:

1. a flexible, elongate tubular member made of shape memory material having a distal end and a proximal end;

2. a preshaped distal end for positioning at a target portion of a cardiac chamber;

3. a shaft at said proximal end of said catheter;

4. an array of spaced-apart electrodes positioned around an outer surface of at least one part of said preshaped distal end; and 5. insulated conductor means electrically connecting the individual electrodes to a means outside of said catheter for selectively mapping and ablating electrically target portions of cardiac tissue adjacent said electrodes in said cardiac chamber.

* * * * *